United States Patent
Koganemaru et al.

(10) Patent No.: US 9,670,219 B2
(45) Date of Patent: Jun. 6, 2017

(54) TETRAHYDROOXEPINOPYRIDINE COMPOUND

(71) Applicant: ASTELLAS PHARMA INC., Chuo-ku (JP)

(72) Inventors: Yohei Koganemaru, Tokyo (JP); Satoshi Miyamoto, Tokyo (JP); Shinya Nagashima, Tokyo (JP); Akio Kamikawa, Tokyo (JP); Koichi Yonezawa, Tokyo (JP); Yuka Koizumi, Tokyo (JP); Satoshi Aoki, Tokyo (JP); Takashi Ogiyama, Tokyo (JP); Shimpei Kawakami, Tokyo (JP); Shigeki Kunikawa, Tokyo (JP); Ryo Sato, Tokyo (JP); Junichi Shishikura, Tokyo (JP); Shuichirou Kakimoto, Tokyo (JP); Hiroshi Yamada, Tokyo (JP); Keisuke Tamaki, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 15/258,241

(22) Filed: Sep. 7, 2016

(65) Prior Publication Data

US 2017/0050973 A1  Feb. 23, 2017

Related U.S. Application Data

(63) Continuation of application No. PCT/JP2016/074145, filed on Aug. 18, 2016.

(30) Foreign Application Priority Data

Aug. 19, 2015 (JP) .................................. 2015-162320

(51) Int. Cl.
*C07D 491/044* (2006.01)
*C07D 519/00* (2006.01)

(52) U.S. Cl.
CPC ....... *C07D 491/044* (2013.01); *C07D 519/00* (2013.01)

(58) Field of Classification Search
CPC .................................................. C07D 491/044
See application file for complete search history.

(56) References Cited

FOREIGN PATENT DOCUMENTS

| WO | WO 2010/020672 A1 | 2/2010 |
| WO | WO 2012/055942 A1 | 5/2012 |
| WO | WO 2012/113850 A2 | 8/2012 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL;http://www.cnn/com/2003/HEALTH/conditions/09/24/alzheimers.drug.ap/index.html>.*
International Search Report and Written Opinion mailed Sep. 27, 2016 (with Partial English Translation).

* cited by examiner

*Primary Examiner* — Rebecca Anderson
(74) *Attorney, Agent, or Firm* — Oblon, McClelland, Maier & Neustadt, L.L.P.

(57) ABSTRACT

[Problem] Provided is a compound having a positive allosteric modulating activity (PAM activity) on an α7 nicotinic acetylcholine receptor (α7 nACh receptor).
[Means for Solution] The present inventors have studied on a PAM activity on an α7 nACh receptor, and they have found that a tetrahydrooxepinopyridine compound has a PAM activity on an α7 nACh receptor, thereby completing the present invention. The tetrahydrooxepinopyridine compound of the present invention has a PAM activity on an α7 nACh receptor and can be expected as an agent for preventing or treating dementia, cognitive impairment, schizophrenia, Alzheimer's disease, CIAS, negative symptoms of schizophrenia, inflammatory diseases, or pain.

16 Claims, No Drawings

TETRAHYDROOXEPINOPYRIDINE COMPOUND

CROSS REFERENCE TO RELATED APPLICATIONS

This application is a continuation of International Patent Application No. PCT/JP2016/074145, filed on Aug. 18, 2016, and claims priority to Japanese Patent Application No. 2015-162320, filed on Aug. 19, 2015.

TECHNICAL FIELD

The present invention relates to a tetrahydrooxepinopyridine compound which has a positive allosteric modulating activity (PAM activity) on an α7 nicotinic acetylcholine receptor (α7 nACh receptor), and can be expected as an active ingredient of a pharmaceutical composition, in particular, a pharmaceutical composition for treating dementia, cognitive impairment, schizophrenia, Alzheimer's disease, cognitive impairment associated with schizophrenia (CIAS), negative symptoms of schizophrenia, inflammatory diseases, or pain.

BACKGROUND ART

The nicotinic acetylcholine receptor (nACh receptor) is a pentamer consisting of five subunits (α, β, γ, ε, or δ) in which these subunits are circularly arranged to constitute an ion channel having cation selectivity (Nature, 2003, vol. 423, pp. 949-955). With regard to the nACh receptor, it is known that there are a plurality of subtypes such as a muscle type (α1β1γδ), a ganglion type (α3β4), and a central nervous system (CNS) type (α7, α4β2). Binding of an endogenous ligand acetylcholine to the nACh receptor leads to opening of an ion channel, which plays an important role in the expression or regulation of various physiological functions such as muscle contraction, inflammation, synaptic transmission and plasticity.

An α7 nACh receptor out of CNS type nACh receptors is present primarily in the cerebral cortex and hippocampus, and is believed to be involved in higher brain functions such as memory and learning. In fact, an α7 nACh receptor agonist has been reported to have various pharmacological effects such as improvement of Alzheimer's disease or CIAS (International Journal of Molecular Sciences, 2012, vol. 13, pp. 2219-2238), improvement of negative symptoms of schizophrenia (The American Journal of Psychiatry, 2008, vol. 165, pp. 1040-1047), inhibition of inflammatory responses (British Journal of Pharmacology, 2007, vol. 151, pp. 915-929), and exhibition of analgesic effects (British Journal of pharmacology, 2012, vol. 167, pp. 421-435). Therefore, a compound stimulating the α7 nACh receptor is considered to be promising as an agent for preventing or treating a disease such as dementia, cognitive impairment, schizophrenia, Alzheimer's disease, CIAS, negative symptoms of schizophrenia, inflammatory diseases, or pain.

On the other hand, it is known that the α7 nACh receptor exhibits higher $Ca^{2+}$ ion permeability and is readily susceptible to desensitization in response to agonist stimulation when compared with other nACh receptor subtypes (Neuron, 1990, vol. 5, pp. 847-856). Therefore, with respect to agonists, there is a possibility of problems associated with attenuation of drug efficacy due to desensitization.

A positive allosteric modulator (PAM) is a group of compounds which themselves have no agonist activity and have an effect of enhancing the intensity of signals transmitted to cells by a receptor. In recent years, drug discovery research on PAMs for an α7 nACh receptor has been energetically proceeding with the aim of improving cognitive impairment seen in Alzheimer's disease patients and schizophrenia patients. In fact, it has become apparent that a plurality of PAMs for an α7 nACh receptor have cognitive function improving effects in various preclinical cognitive models (Biochemical Pharmacology, 2007, vol. 74, pp. 1155-1163). From the foregoing, it can be expected that PAMs for an α7 nACh receptor will become a drug for preventing or treating dementia, cognitive impairment, schizophrenia, Alzheimer's disease, CIAS, negative symptoms of schizophrenia, inflammatory diseases, or pain.

Up to now, compounds controlling an α7 nACh receptor have been reported.

Patent Document 1 discloses that a compound represented by the following general formula or a pharmaceutically acceptable salt thereof is a modulator of an nACh receptor, and there is a description regarding use in the treatment of diseases associated with cholinergic neurons in the CNS or peripheral nervous system (PNS).

[Chem. 1]

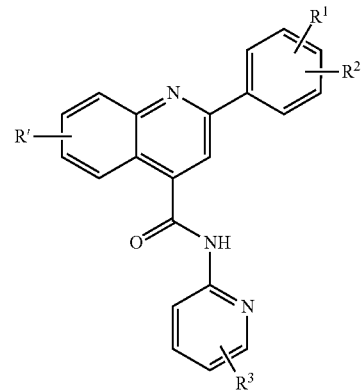

(For symbols in the formula, refer to Patent Document 1)

Patent Document 2 discloses that a compound represented by the following general formula or a pharmaceutically acceptable salt thereof is an α7 nACh receptor modulator, and there is a description regarding use in the treatment of pain, psychotic disorder, cognitive impairment, or Alzheimer's disease.

[Chem. 2]

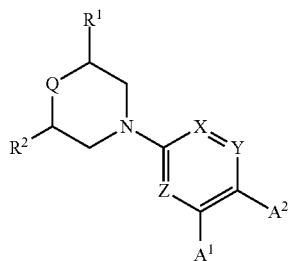

(In the formula, each of X, Y or Z is selected from CH and N. For the other symbols, refer to Patent Document 2)

Patent Document 3 discloses that a compound represented by the following general formula, an optical isomer, or acid addition salt thereof is a PAM of nACh receptors.

[Chem. 3]

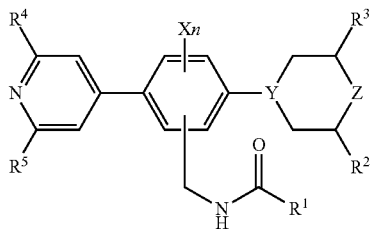

(In the formula, X is fluoro or chloro; and n is 0, 1 or 2. For the other symbols, refer to Patent Document 3)

RELATED ART

Patent Document

[Patent Document 1] WO 2010/020672
[Patent Document 2] WO 2012/055942
[Patent Document 3] WO 2012/113850

DISCLOSURE OF INVENTION

Problems to be Solved by the Invention

Provided is a compound which has a PAM activity on an α7 nACh receptor, and can be expected as an active ingredient of a pharmaceutical composition, in particular, a pharmaceutical composition for preventing or treating dementia, cognitive impairment, schizophrenia, Alzheimer's disease, CIAS, negative symptoms of schizophrenia, inflammatory diseases, or pain.

Means for Solving the Problems

The present inventors have conducted extensive studies on a compound having a PAM activity on an α7 nACh receptor, and as a result, they have found that the tetrahydrooxepinopyridine compound of the present invention has a PAM activity on an α7 nACh receptor, thereby completing the present invention.

That is, the present invention relates to a compound of the formula (I) or a salt thereof, as well as a pharmaceutical composition comprising a compound of the formula (I) or a salt there of and a pharmaceutically acceptable excipient.

[Chem. 4]

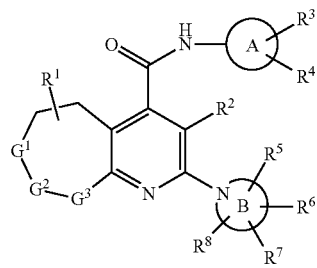

(I)

(In the formula,
$R^1$ is H or lower alkyl,
$R^2$ is H or CN,
any one of $G^1$, $G^2$, and $G^3$ is O, and the other two of $G^1$, $G^2$, and $G^3$ are $CH_2$,
ring A is aryl, or nitrogen-containing heteroaryl,
ring B is cyclic amino,
$R^3$ and $R^4$ are the same as or different each other, and are H, halogen, lower alkyl, -lower alkylene-OH, halo-lower alkyl, —O-lower alkyl, —O-halo-lower alkyl, cycloalkyl, CN, OH, —N(lower alkyl)$_2$, or —C(=O)NH$_2$,
$R^5$, $R^6$, $R^7$ and $R^8$ are the same as or different from each other, and are H, halogen, lower alkyl, halo-lower alkyl, —O-lower alkyl, or CN, or
in the case where $R^5$ and $R^6$ are bonded to the same carbon atom, $R^5$ and $R^6$ may form cycloalkane or cyclic ether together with the carbon atom, and may form a spiro ring together with Ring B, or
ring B may form 6,7-dihydro[1,3]oxazolo[4,5-c]pyridin-5(4H)-yl together with $R^5$ and $R^6$.)

In addition, unless otherwise specified, when symbols in a certain chemical formula in the present specification are also used in another chemical formula, the same symbol represents the same meaning.

Moreover, the present invention relates to:
(1) a pharmaceutical composition comprising a compound of the formula (I) or a salt thereof, which is a positive allosteric modulator on an α7 nicotinic acetylcholine receptor; and
(2) a pharmaceutical composition for preventing or treating dementia, cognitive impairment, schizophrenia, Alzheimer's disease, CIAS, negative symptoms of schizophrenia, inflammatory diseases, or pain, comprising a compound of the formula (I) or a salt thereof.
(3) Here, the pharmaceutical composition includes an agent for preventing or treating dementia, cognitive impairment, schizophrenia, Alzheimer's disease, CIAS, negative symptoms of schizophrenia, inflammatory diseases, or pain, comprising a compound of the formula (I) or a salt thereof.

Further, the present invention relates to:
(4) use of a compound of the formula (I) or a salt thereof for the manufacture of a pharmaceutical composition for preventing or treating dementia, cognitive impairment, schizophrenia, Alzheimer's disease, CIAS, negative symptoms of schizophrenia, inflammatory diseases, or pain;
(5) use of a compound of the formula (I) or a salt thereof for preventing or treating dementia, cognitive impairment, schizophrenia, Alzheimer's disease, CIAS, negative symptoms of schizophrenia, inflammatory diseases, or pain;
(6) a compound of the formula (I) or a salt thereof for preventing or treating dementia, cognitive impairment, schizophrenia, Alzheimer's disease, CIAS, negative symptoms of schizophrenia, inflammatory diseases, or pain; and
(7) a method for preventing or treating dementia, cognitive impairment, schizophrenia, Alzheimer's disease, CIAS, negative symptoms of schizophrenia, inflammatory diseases, or pain, comprising administering to a subject an effective amount of a compound of the formula (I) or a salt thereof.

Meanwhile, the term "subject" is a human being or another animal in need of prevention or treatment thereof, and according to one embodiment, a human being in need of prevention or treatment thereof.

Effects of the Invention

A compound of the formula (I) or a salt thereof has a PAM activity on an α7 nACh receptor, and can be expected to be used as an agent for preventing or treating dementia, cognitive impairment, schizophrenia, Alzheimer's disease, CIAS, negative symptoms of schizophrenia, inflammatory diseases, or pain.

EMBODIMENTS FOR CARRYING OUT THE INVENTION

Hereinafter, the present invention will be described in detail.

As used herein, the term "lower alkyl" is a linear or branched alkyl having 1 to 6 carbon atoms (hereinafter, also referred to as $C_{1-6}$ alkyl). For example, the lower alkyl is methyl, ethyl, n-propyl, isopropyl, n-butyl, or the like. In one embodiment, the lower alkyl is $C_{1-2}$ alkyl. In one embodiment, the lower alkyl is methyl.

The "lower alkylene" is a linear or branched $C_{1-6}$ alkylene (hereinafter, also referred to as $C_{1-6}$ alkylene), for example, methylene, ethylene, propylene, —$C(CH_3)_2$—, or the like; and in one embodiment, —$C(CH_3)_2$—.

The "halogen" is F, Cl, Br, or I; and in one embodiment, F.

The "halo-lower alkyl" is $C_{1-6}$ alkyl substituted with one or more halogen atoms; in one embodiment, $C_{1-6}$ alkyl substituted with 1 to 5 halogen atoms; in one embodiment, $C_{1-6}$ alkyl substituted with 1 to 3 halogen atoms; in one embodiment, $CF_3$ or $CHF_2$; and in one embodiment, $CF_3$.

The "cycloalkane" is a saturated hydrocarbon ring having 3 to 7 ring atoms (hereinafter, also referred to as $C_{3-7}$ cycloalkane), for example, cyclopropane, cyclobutane, cyclopentane, cyclohexane, cycloheptane, or the like; in one embodiment, $C_{3-6}$-cycloalkane; and in one embodiment, cyclopropane.

The "cycloalkyl" is a saturated hydrocarbon ring group having 3 to 7 ring atoms (hereinafter, also referred to as $C_{3-7}$ cycloalkyl), for example, cyclopropyl, cyclobutyl, cyclopentyl, cyclohexyl, cycloheptyl, or the like; in one embodiment, $C_{3-6}$ cycloalkyl; and in one embodiment, cyclopropyl.

The "cyclic amino" is a group in which one or more ring atoms are substituted with nitrogen atoms in cycloalkyl having 5 to 7 ring atoms, which has a bond on one of the nitrogen atoms. Here, some of carbon atoms of ring atoms may be substituted with oxygen atoms. In one embodiment, the cyclic amino is 5- or 6-membered cyclic amino; in one embodiment, a group of the formula (IIa):

[Chem. 5]

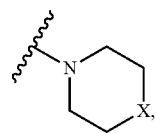

(IIa)

wherein X is $CH_2$, O, or a bond; in one embodiment, a group of the formula (IIa) wherein X is $CH_2$ or O; in one embodiment, a group of the formula (IIa) wherein X is $CH_2$ or a bond; in one embodiment, a group of the formula (IIa) wherein X is $CH_2$; in one embodiment, a group of the formula (IIa) wherein X is O; and in one embodiment, a group of the formula (IIa) wherein X is a bond.

The "cyclic ether" is a saturated ring having 3 to 8 ring atoms and containing only 1 or 2 oxygen atoms as a heteroatom, for example, oxirane, oxetane, oxolane, dioxolane, oxane, dioxane, oxepane, oxocane, or the like; in one embodiment, 3- to 6-membered cyclic ether; and in one embodiment, oxetane.

The "aryl" is an aromatic hydrocarbon ring group formed by removing one hydrogen atom from a monocyclic or bicyclic aromatic hydrocarbon ring having 6 to 10 carbon atoms (hereinafter, also referred to as $C_{6-10}$ aryl), for example, phenyl or naphthyl; and in one embodiment, phenyl.

The "nitrogen-containing heteroaryl" is a group formed by removing one hydrogen atom from a monocyclic or bicyclic aromatic hetero ring, which has one or more nitrogen atoms as ring atoms and may further have one or more oxygen atoms or sulfur atoms as ring atoms. Examples thereof include (a) oxazolyl, isoxazolyl, isothiazolyl, thiazolyl, imidazolyl, pyrazolyl, oxadiazolyl, thiadiazolyl, tetrazolyl, triazolyl, and the like; (b) pyridyl, pyridazinyl, pyrimidinyl, pyrazinyl, and the like; and (c) benzothiazolyl, benzimidazolyl, thiazolopyridyl, and the like.

The "nitrogen-containing monocyclic heteroaryl" is a monocyclic nitrogen-containing heteroaryl, for example, the above (a) or (b).

The "nitrogen-containing 5-membered heteroaryl" is 5-membered nitrogen-containing heteroaryl, for example, the above (a).

The "nitrogen-containing 6-membered heteroaryl" is 6-membered nitrogen-containing heteroaryl, for example, the above (b).

The "nitrogen-containing bicyclic heteroaryl" is bicyclic nitrogen-containing heteroaryl, for example, the above (c).

One embodiment of the "nitrogen-containing heteroaryl" may be shown below. An example thereof is nitrogen-containing monocyclic heteroaryl, or nitrogen-containing bicyclic heteroaryl; in one embodiment, nitrogen-containing monocyclic heteroaryl, or nitrogen-containing bicyclic heteroaryl in which nitrogen-containing monocyclic heteroaryl is fused with a benzene ring or a pyridine ring; in one embodiment, nitrogen-containing monocyclic heteroaryl; in one embodiment, nitrogen-containing 6-membered heteroaryl; in one embodiment, nitrogen-containing 6-membered heteroaryl having one or two nitrogen atoms as ring atoms; in one embodiment, nitrogen-containing 6-membered heteroaryl having two nitrogen atoms as ring atoms; in one embodiment, pyridyl, pyridazinyl or pyrazinyl; in one embodiment, pyridyl, pyridazinyl; and in one embodiment, pyridazinyl.

One embodiment of the present invention is shown below. In the present specification, particularly in terms of embodiments, "a compound of the formula (I) or a salt thereof" may be simply referred to as "a compound of the formula (I)" in some cases. In the present specification, particularly in terms of embodiments, "a compound or a salt thereof" may be simply referred to as "a compound" in some cases.

(1) A compound of the formula (I) wherein $R^1$ is H.
(2) A compound of the formula (I) wherein $R^2$ is H.
(3) A compound of the formula (I) wherein $G^1$ is O, and $G^2$ and $G^3$ are $CH_2$.
(4) A compound of the formula (I) wherein ring A is phenyl or nitrogen-containing heteroaryl. In one embodiment, a compound of the formula (I) wherein ring A is phenyl, nitrogen-containing monocyclic heteroaryl, or nitrogen-containing bicyclic heteroaryl. In one embodiment, a compound of the formula (I) wherein ring A is nitrogen-containing monocyclic heteroaryl. In one embodiment, a compound of the formula (I) wherein ring A is nitrogen-containing 6-membered heteroaryl having one or two nitrogen atoms as ring atoms. In one embodiment, a compound of the formula (I) wherein ring A is pyridyl. In one embodiment, a compound of the formula (I) wherein ring A is nitrogen-containing 6-membered heteroaryl having two nitrogen atoms as ring atoms.

(5) A compound of the formula (I) wherein ring B is 5- or 6-membered cyclic amino.

(5-1) A compound of the formula (I) wherein ring B and $R^5$, $R^6$, $R^7$, and $R^8$ (hereinafter, also referred to as $R^5$ to $R^8$) are the formula (II):

[Chem. 6]

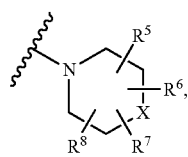

(II)

X is $CH_2$, O, or a bond, and in the case where X is $CH_2$, $R^5$ and $R^6$ may be substituted with X. In one embodiment, a compound of the formula (I) wherein ring B and $R^5$ to $R^8$ are the formula (II), and X is $CH_2$, O, or a bond. In one embodiment, a compound of the formula (I) wherein ring B and $R^5$ to $R^8$ are the formula (II), and in the case where X is $CH_2$, $R^5$ and $R^6$ are substituted with X. In one embodiment, a compound of the formula (I) wherein ring B and $R^5$ to $R^8$ are the formula (II), and X is $CH_2$ or O. In one embodiment, a compound of the formula (I) wherein ring B and $R^5$ to $R^8$ are the formula (II), and X is O. In one embodiment, a compound of the formula (I) wherein ring B and $R^5$ to $R^8$ are the formula (II), and X is $CH_2$. In one embodiment, a compound of the formula (I) wherein ring B and $R^5$ to $R^8$ are the formula (II), and X is bond.

(5-2) A compound of the formula (I) wherein ring B and $R^5$ to $R^8$ are the formula (III):

[Chem. 7]

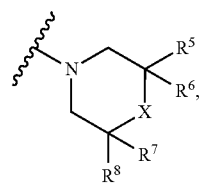

(III)

and X is $CH_2$, O, or a bond. In one embodiment, a compound of the formula (I) wherein ring B and $R^5$ to $R^8$ are the formula (III), and X is $CH_2$ or O. In one embodiment, a compound of the formula (I) wherein ring B and $R^5$ to $R^8$ are the formula (III), and X is O. In one embodiment, a compound of the formula (I) wherein ring B and $R^5$ to $R^8$ are the formula (III), and X is $CH_2$.

(5-3) A compound of the formula (I) wherein ring B and $R^5$ to $R^8$ are the formula (IV) or the formula (V):

[Chem. 8]

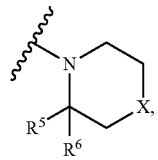

(IV)

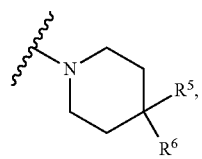

(V)

and X is $CH_2$ or a bond. In one embodiment, a compound of the formula (I) wherein ring B and $R^5$ to $R^8$ are the formula (IV) or the formula (V), and X is a bond. In one embodiment, a compound of the formula (I) wherein ring B and $R^5$ to $R^8$ are the formula (IV) or the formula (V), and X is $CH_2$. In one embodiment, a compound of the formula (I) wherein ring B and $R^5$ to $R^8$ are the formula (IV), and X is $CH_2$ or a bond. In one embodiment, a compound of the formula (I) wherein ring B and $R^5$ to $R^8$ are the formula (IV), and X is a bond. In one embodiment, a compound of the formula (I) wherein ring B and $R^5$ to $R^8$ are the formula (IV), and X is $CH_2$. In one embodiment, a compound of the formula (I) wherein ring B and $R^5$ to $R^8$ is the formula (V).

(5-4) A compound of the formula (I) wherein ring B and $R^5$ to $R^8$ are the formula (VI):

[Chem. 9]

(VI)

and X is $CH_2$ or O. In one embodiment, a compound of the formula (I) wherein ring B and $R^5$ to $R^8$ are the formula (VI), and X is O.

(5-5) A compound of the formula (I) wherein ring B forms 6,7-dihydro[1,3]oxazolo[4,5-c]pyridin-5(4H)-yl together with $R^5$ and $R^6$.

(6) A compound of the formula (I) wherein $R^3$ is H, halogen, lower alkyl, -lower alkylene-OH, halo-lower alkyl, —O-lower alkyl, —O-halo-lower alkyl, cycloalkyl, CN, OH, —N(lower alkyl)$_2$, or —C(=O)NH$_2$. In one embodiment, a compound of the formula (I) wherein $R^3$ is H or lower alkyl. In one embodiment, a compound of the formula (I) wherein $R^3$ is H. In one embodiment, a compound of the formula (I) wherein $R^3$ is lower alkyl.

(7) A compound of the formula (I) wherein $R^4$ is H, halogen, lower alkyl, -lower alkylene-OH, halo-lower alkyl, —O-lower alkyl, —O-halo-lower alkyl, cycloalkyl, CN, OH, —N(lower alkyl)$_2$, or —C(=O)NH$_2$. In one embodiment, a compound of the formula (I) wherein $R^4$ is H, halogen, lower alkyl, -lower alkylene-OH, halo-lower alkyl, —O-lower alkyl, cycloalkyl or CN. In one embodiment, a compound of the formula (I) wherein $R^4$ is halogen, lower alkyl, -lower alkylene-OH, halo-lower alkyl, —O-lower alkyl, cycloalkyl or CN. In one embodiment, a compound of the formula (I) wherein $R^4$ is H, halogen, lower alkyl, or —O-lower alkyl. In one embodiment, a compound of the formula (I) wherein $R^4$ is halogen, lower alkyl, or —O-lower alkyl. In one embodiment, a compound of the formula (I) wherein $R^4$ is H or halogen. In one embodiment, a compound of the formula (I) wherein $R^4$ is H. In one embodiment, a compound of the formula (I) wherein $R^4$ is halogen. In one embodiment, a compound of the formula (I) wherein $R^4$ is lower alkyl. In one embodiment, the compound of the formula (I) wherein $R^4$ is —O-lower alkyl.

(8) A compound of the formula (I) wherein $R^5$ is H, halogen, lower alkyl, halo-lower alkyl, —O-lower alkyl, or CN. In one embodiment, a compound of the formula (I) wherein $R^5$ is H, halogen, lower alkyl, or halo-lower alkyl. In one embodiment, a compound of the formula (I) wherein $R^5$ is halogen or lower alkyl. In one embodiment, a compound of the formula (I) wherein $R^5$ is halogen. In one embodiment, a compound of the formula (I) wherein $R^5$ is lower alkyl. In one embodiment, a compound of the formula (I) wherein $R^5$ is halo-lower alkyl. In one embodiment, a compound of the formula (I) wherein $R^5$ is $CH_3$.

(9) A compound of the formula (I) wherein $R^6$ is H, halogen, lower alkyl, halo-lower alkyl, —O-lower alkyl, or CN. In one embodiment, a compound of the formula (I) wherein $R^6$ is H, halogen, lower alkyl, or halo-lower alkyl. In one embodiment, a compound of the formula (I) wherein $R^6$ is H or lower alkyl. In one embodiment, a compound of the formula (I) wherein $R^6$ is lower alkyl. In one embodiment, a compound of the formula (I) wherein $R^6$ is H.

(10) A compound of the formula (I) wherein in the case where $R^5$ and $R^6$ are bonded to the same carbon atom, $R^5$ and $R^6$ form cycloalkane or cyclic ether together with the carbon atom, and form a spiro ring together with ring B. In one embodiment, a compound of the formula (I) wherein in the case where $R^5$ and $R^6$ are bonded to the same carbon atom, $R^5$ and $R^6$ form $C_{3-6}$ cycloalkane or 3- to 6-membered cyclic ether together with the carbon atom, and form a spiro ring together with ring B. In one embodiment, a compound of the formula (I) wherein in the case where $R^5$ and $R^6$ are bonded to the same carbon atom, $R^5$ and $R^6$ form cycloalkane together with the carbon atom.

(11) A compound of the formula (I) wherein $R^7$ is H, halogen, lower alkyl, halo-lower alkyl, —O-lower alkyl, or CN. In one embodiment, a compound of the formula (I) wherein $R^7$'s are the same as or different from each other, and are H, halogen, lower alkyl, or halo-lower alkyl. In one embodiment, a compound of the formula (I) wherein $R^7$ is H or lower alkyl. In one embodiment, a compound of the formula (I) wherein $R^7$ is lower alkyl. In one embodiment, a compound of the formula (I) wherein $R^7$ is H.

(12) A compound of the formula (I) wherein $R^8$ is H, halogen, lower alkyl, halo-lower alkyl, —O-lower alkyl, or CN. In one embodiment, a compound of the formula (I) wherein $R^8$ is H, halogen, lower alkyl, or halo-lower alkyl. In one embodiment, a compound of the formula (I) wherein $R^8$ is H or lower alkyl. In one embodiment, a compound of the formula (I) wherein $R^8$ is lower alkyl. In one embodiment, a compound of the formula (I) wherein $R^8$ is $CH_3$. In one embodiment, a compound of the formula (I) wherein $R^8$ is H.

(13) The compound of the formula (I) which is a non-contradictory combination of two or more of the groups described in the above (1) to (12).

Examples of the combination described in the above (13) include the following embodiments.

(14) A compound of the formula (I) wherein $R^3$ and $R^4$ are the same as or different from each other, and are H, halogen, lower alkyl, -lower alkylene-OH, halo-lower alkyl, —O-lower alkyl, —O-halo-lower alkyl, cycloalkyl, CN, OH, —N(lower alkyl)$_2$, or —C(=O)NH$_2$.

(15) A compound of the formula (I) wherein $R^5$ to $R^8$ are the same as or different from each other, and are H, halogen, lower alkyl, halo-lower alkyl, —O-lower alkyl, or CN, or
in the case where $R^5$ and $R^6$ are bonded to the same carbon atom, $R^5$ and $R^6$ may form $C_{3-6}$ cycloalkane or 3- to 6-membered cyclic ether together with the carbon atom, and may form a spiro ring together with ring B, or
ring B may form 6,7-dihydro[1,3]oxazolo[4,5-c]pyridin-5(4H)-yl together with $R^5$ and $R^6$.

(16) A compound of the formula (I) wherein $R^5$ to $R^8$ are the same as or different from each other, and are H, halogen, lower alkyl, halo-lower alkyl, —O-lower alkyl, or CN, A compound of the formula (I) wherein $R^5$ to $R^8$ are the same as or different from each other, and are H, halogen, lower alkyl, or halo-lower alkyl. A compound of the formula (I) wherein $R^5$ to $R^8$ are the same as or different from each other, and are H, lower alkyl, or halo-lower alkyl.

(17) A compound of the formula (I) wherein $R^5$ is halo-lower alkyl, and $R^6$, $R^7$, and $R^8$ are H. In one embodiment, a compound of the formula (I) wherein $R^5$, $R^6$, $R^7$ and $R^8$ are lower alkyl. In one embodiment, a compound of the formula (I) wherein $R^5$ and $R^8$ are lower alkyl, and $R^6$ and $R^7$ are H. In one embodiment, a compound of the formula (I) wherein $R^5$ and $R^8$ are $CH_3$, and $R^6$ and $R^7$ are H.

Further, specific examples of the combination described in the above (13) include the following embodiments.

(A) A compound of the formula (I) wherein $R^1$ is H, $R^2$ is H, $G^1$ is O, each of $G^2$ and $G^3$ is $CH_2$, ring A is pyridyl, ring B and $R^5$ to $R^8$ are the formula (III), X is O, $R^3$ is H, $R^4$ is halogen, $R^5$ is lower alkyl, $R^6$ is H, $R^7$ is H, and $R^8$ is lower alkyl.

(B) A compound of the formula (I) wherein $R^1$ is H, $R^2$ is H, $G^1$ is O, each of $G^2$ and $G^3$ is $CH_2$, ring A is pyridyl, ring B and $R^5$ to $R^8$ are the formula (III), X is O, $R^3$ is H, $R^4$ is lower alkyl, $R^5$ is lower alkyl, $R^6$ is H, $R^7$ is H, and $R^8$ is H.

(C) A compound of the formula (I) wherein $R^1$ is H, $R^2$ is H, $G^1$ is O, each of $G^2$ and $G^3$ is $CH_2$, ring A is nitrogen-containing 6-membered heteroaryl having two nitrogen atoms as ring atoms, ring B and $R^5$ to $R^8$ are the formula (IV), X is a bond, $R^3$ is H or lower alkyl, $R^4$ is lower alkyl or —O-lower alkyl, $R^5$ is lower alkyl, $R^6$ is H, $R^7$ is H, and $R^8$ is H.

(D) A compound of the formula (I) wherein $R^1$ is H, $R^2$ is H, $G^1$ is O, each of $G^2$ and $G^3$ is $CH_2$, ring A is nitrogen-containing 6-membered heteroaryl having two nitrogen atoms as ring atoms, ring B and $R^5$ to $R^8$ are the formula (IV), X is a bond, $R^3$ is H, $R^4$ is —O-lower alkyl, $R^5$ is lower alkyl, $R^6$ is H, $R^7$ is H, and $R^8$ is H.

(E) A compound of the formula (I) wherein $R^1$ is H, $R^2$ is H, $G^1$ is O, each of $G^2$ and $G^3$ is $CH_2$, ring A is nitrogen-containing 6-membered heteroaryl having two nitrogen atoms as ring atoms, ring B and $R^5$ to $R^8$ are the formula (IV), X is a bond, $R^3$ is H, $R^4$ is lower alkyl, $R^5$ is lower alkyl, $R^6$ is H, $R^7$ is H, and $R^8$ is H.

(F) A compound of the formula (I) wherein $R^1$ is H, $R^2$ is H, $G^1$ is O, each of $G^2$ and $G^3$ is $CH_2$, ring A is nitrogen-containing 6-membered heteroaryl having two nitrogen atoms as ring atoms, ring B and $R^5$ to $R^8$ are the formula (IV), X is a bond, $R^3$ is lower alkyl, $R^4$ is lower alkyl, $R^5$ is lower alkyl, $R^6$ is H, $R^7$ is H, and $R^8$ is H.

(G) A compound of the formula (I) wherein $R^1$ is H, $R^2$ is H, $G^1$ is O, each of $G^2$ and $G^3$ is $CH_2$, ring A is nitrogen-containing 6-membered heteroaryl having two nitrogen atoms as ring atoms, ring B and $R^5$ to $R^8$ are a group of the formula (V), $R^3$ is H, $R^4$ is H, $R^5$ is halogen, and each of $R^6$, $R^7$ and $R^8$ is H.

(H) A compound of the formula (I) wherein $R^1$ is H, $R^2$ is H, $G^1$ is O, each of $G^2$ and $G^3$ is $CH_2$, ring A is nitrogen-containing 6-membered heteroaryl having two nitrogen atoms as ring atoms, ring B and $R^5$ to $R^8$ are the formula (III), X is $CH_2$, $R^3$ is H, $R^4$ is H, $R^5$ is lower alkyl, $R^6$ is H, $R^7$ is H, and $R^8$ is lower alkyl.

(I) A compound of the formula (I) wherein $R^1$ is H, $R^2$ is H, $G^1$ is O, each of $G^2$ and $G^3$ is $CH_2$, ring A is pyridyl, ring B and $R^5$ to $R^8$ are the formula (III), X is O, $R^3$ is H, $R^4$ is halogen, $R^5$ is halogen, $R^6$ is H, $R^7$ is H, and $R^8$ is H.

Further, other specific examples of the combination of the above (13) include the following embodiments.

[1] A compound of the formula (I) wherein $R^1$ is H, $R^2$ is H, $G^1$ is O, each of $G^2$ and $G^3$ is $CH_2$, ring A is phenyl or nitrogen-containing heteroaryl, and ring B is 5- or 6-membered cyclic amino.

[2] The compound according to [1], wherein ring A is nitrogen-containing monocyclic heteroaryl, $R^3$ is H or lower alkyl, $R^4$ is H, halogen, lower alkyl, -lower alkylene-OH, halo-lower alkyl, —O-lower alkyl, —O-halo-lower alkyl, cycloalkyl, CN, OH, —N(lower alkyl)$_2$, or —C(=O)NH$_2$, and $R^5$ to $R^8$ are the same as or different from each other, and are H, halogen, lower alkyl, halo-lower alkyl, —O-lower alkyl, or CN.

[2-1] The compound according to [1], wherein ring A is nitrogen-containing monocyclic heteroaryl, $R^3$ is H or lower alkyl, $R^4$ is H, halogen, lower alkyl, -lower alkylene-OH, halo-lower alkyl, —O-lower alkyl, cycloalkyl, or CN.

[2-2] The compound according to [1], wherein ring A is nitrogen-containing monocyclic heteroaryl, $R^3$ is H or lower alkyl, $R^4$ is H, halogen, lower alkyl, or —O-lower alkyl.

[3] The compound according to [1] or [2], wherein ring B and $R^5$ to $R^8$ are the formula (II), X is $CH_2$, O, or a bond, in the case where X is $CH_2$, $R^5$ and $R^6$ may be substituted with X, and $R^5$ to $R^8$ are the same as or different from each other, and are H, halogen, lower alkyl, or halo-lower alkyl.

[4] The compound according to [3], wherein X is $CH_2$ or O.

[5] The compound according to [3], wherein X is bond.

[6] The compound according to [4], wherein ring A is nitrogen-containing 6-membered heteroaryl having one or two nitrogen atoms as ring atoms, ring B and $R^5$ to $R^8$ are the formula (III), $R^5$ is halogen or lower alkyl, $R^6$ is H, $R^7$ is H, and $R^8$ is H or lower alkyl.

[7] The compound according to [6], wherein ring A is pyridyl, X is $CH_2$, $R^5$ is halogen, and $R^8$ is H.

[8] The compound according to [6], wherein ring A is pyridyl, X is O, $R^5$ is lower alkyl, and $R^8$ is lower alkyl.

[9] The compound according to [5], wherein ring A is nitrogen-containing 6-membered heteroaryl having two nitrogen atoms as ring atoms, ring B and $R^5$ to $R^8$ are the formula (IV), $R^5$ is halogen or lower alkyl, $R^6$ is H, $R^7$ is H, and $R^8$ is H.

[10] The compound according to [1], wherein ring B and $R^5$ to $R^8$ are the formula (II), X is $CH_2$ or O.

[11] The compound according to [10], wherein ring A, $R^3$, $R^4$ and $R^5$ to $R^8$ are each of the groups described in [2].

[12] The compound according to [11], $R^5$ to $R^8$ are the same as or different from each other, and are H, halogen, lower alkyl, or halo-lower alkyl.

[13] The compound according to [12], wherein $R^3$ is H or lower alkyl, $R^4$ is H, halogen, lower alkyl, or —O-lower alkyl.

[14] The compound according to [13], wherein ring B and $R^5$ to $R^8$ are the formula (III).

[15] The compound according to [1], wherein ring B and $R^5$ to $R^8$ are the formula (II), X is bond.

[16] The compound according to [15], wherein ring A, $R^3$, $R^4$ and $R^5$ to $R^8$ are each of the groups described in [2].

[17] The compound according to [16], $R^5$ to $R^8$ are the same as or different from each other, and are H, halogen, lower alkyl, or halo-lower alkyl.

[18] The compound according to [17], wherein $R^3$ is H or lower alkyl, $R^4$ is H, halogen, lower alkyl, or —O-lower alkyl.

[19] The compound according to [18], wherein ring B and $R^5$ to $R^8$ are the formula (IV).

[20] The compound according to any one of [3] to [19], wherein [2] is [2-1] or [2-2].

[21] The compound according to any one of [1] to [20], wherein X is $CH_2$.

[22] The compound according to any one of [1] to [20], wherein X is O.

Further, still other specific examples of the combination of the above (13) include the following embodiments.

[a] A compound of the formula (I) wherein $R^5$ to $R^8$ are the same as or different from each other, and are H, halogen, lower alkyl, or halo-lower alkyl,
wherein $R^5$ and $R^6$, taken together with the same carbon atom to which they are bonded, may form cycloalkane.

[b] The compound according to [a], wherein $G^1$ is O, $G^2$ and $G^3$ are $CH_2$, ring B and $R^5$ to $R^8$ are the formula (II), and X is $CH_2$ or O.

[c] The compound according to [b], wherein ring B and $R^5$ to $R^8$ are the formula (III), and X is $CH_2$ or O.

[d] The compound according to [c], wherein ring A is phenyl or nitrogen-containing monocyclic heteroaryl, and the nitrogen-containing monocyclic heteroaryl is a group which may be fused with a benzene ring or a pyridine ring.

[e] The compound according to [d], wherein $R^1$ is H, and $R^2$ is H.

[f] The compound according to [e], wherein $R^3$ and $R^4$ are the same as or different from each other, and are H, halogen, lower alkyl, -lower alkylene-OH, halo-lower alkyl, —O-lower alkyl, —O-halo-lower alkyl, $C_{3-6}$ cycloalkyl or CN, and $R^5$ to $R^8$ are the same as or different from each other, and are H, lower alkyl, or halo-lower alkyl.

[g] The compound according to [f], wherein $R^1$ is H, $R^2$ is H, $G^1$ is O, $G^2$ and $G^3$ are $CH_2$, ring A is nitrogen-containing 6-membered heteroaryl having one or two nitrogen atoms, ring B and $R^5$ to $R^8$ are the formula (III), X is O, $R^3$ is H, $R^4$ is H or halogen, and $R^5$ to $R^8$ are the same as or different from each other, and are H, lower alkyl, or halo-lower alkyl.

[h] The compound according to [g], wherein ring B and $R^5$ to $R^8$ are the formula (VI), one of $R^5$ and $R^6$ is halo-lower alkyl and the other one is H, and $R^7$ and $R^8$ are H.

[i] The compound according to [g], wherein ring B and $R^5$ to $R^8$ are the formula (VI), and $R^5$, $R^6$, $R^7$, and $R^8$ are lower alkyl.

[j] The compound according to [g], wherein ring B and $R^5$ to $R^8$ are the formula (VI), $R^5$ and $R^8$ are lower alkyl, and $R^6$ and $R^7$ are H.

Specific examples of the compound encompassed by the present invention include compounds of the formula (I) or salts thereof selected from the group consisting of the following.

N-(pyridazin-3-yl)-2-[(3S)-3-(trifluoromethyl)piperidin-1-yl]-5,6,8,9-tetrahydrooxepino[4,5-b]pyridine-4-carboxamide, N-(pyridazin-3-yl)-2-[(3R)-3-(trifluoromethyl)piperidin-1-yl]-5,6,8,9-tetrahydrooxepino[4,5-b]pyridine-4-carboxamide, N-(pyridazin-3-yl)-2-(2,2,6,6-tetramethylmorpholin-4-yl)-5,6,8,9-tetrahydrooxepino[4,5-b]pyridine-4-carboxamide, 2-[(2R,6S)-2,6-dimethylmorpholin-4-yl]-N-(5-fluoropyridin-2-yl)-5,6,8,9-tetrahydrooxepino[4,5-b]pyridine-4-carboxamide, N-(5-chloropyridin-2-yl)-2-[(2R,6S)-2,6-dimethylmorpholin-4-yl]-5,6,8,9-tetrahydrooxepino[4,5-b]pyridine-4-carboxamide, N-(6-methoxypyridazin-3-yl)-2-[(2R)-2-methylpyrrolidin-1-yl]-5,6,8,9-tetrahydrooxepino[4,5-b]pyridine-4-carboxamide, N-(6-methylpyrazin-2-yl)-2-[(2S)-2-methylpyrrolidin-1-yl]-5,6,8,9-tetrahydrooxepino[4,5-b]pyridine-4-carboxamide, 2-[(2R)-2-ethylmorpholin-4-yl]-N-(6-methylpyridin-3-yl)-5,6,8,9-tetrahydrooxepino[4,5-b]pyridine-4-carboxamide, N-(5,6-dimethylpyrazin-2-yl)-2-[(2R)-2-methylpyrrolidin-1-yl]-5,6,8,9-tetrahydrooxepino[4,5-b]pyridine-4-carboxamide, N-(3-cyanophenyl)-2-[(3S)-3-methoxypyrrolidin-1-yl]-5,6,8,9-tetrahydrooxepino[4,5-b]pyridine-4-carboxamide, 2-(4-fluoropiperidin-1-yl)-N-(pyridazin-3-yl)-5,6,8,9-tetrahydrooxepino[4,5-b]pyridine-4-carboxamide, N-(5-chloropyridin-2-yl)-2-(4-fluoropiperidin-1-yl)-5,6,8,9-tetrahydrooxepino[4,5-b]pyridine-4-carboxamide, N-(5,6-dimethylpyrazin-2-yl)-2-[(2S)-2-methylpyrrolidin-1-yl]-5,6,8,9-tetrahydrooxepino[4,5-b]pyridine-4-carboxamide, 2-[(2S)-2-methylpiperidin-1-yl]-N-(pyridazin-3-yl)-5,6,8,9-tetrahydrooxepino[4,5-b]pyridine-4-carboxamide, 2-[(2S)-2-methylpiperidin-1-yl]-N-(pyrazin-2-yl)-5,6,8,9-tetrahydrooxepino[4,5-b]pyridine-4-carboxamide, and N-(5-chloropyridin-2-yl)-2-[(3S)-3-fluoropiperidin-1-yl]-5,6,8,9-tetrahydrooxepino[4,5-b]pyridine-4-carboxamide.

Specific examples of the compound encompassed by the present invention include compounds of the formula (I) or salts thereof selected from the group consisting of the following.

N-(pyridazin-3-yl)-2-[(3S)-3-(trifluoromethyl)piperidin-1-yl]-5,6,8,9-tetrahydrooxepino[4,5-b]pyridine-4-carboxamide fumarate, N-(pyridazin-3-yl)-2-[(3R)-3-(trifluoromethyl)piperidin-1-yl]-5,6,8,9-tetrahydrooxepino[4,5-b]pyridine-4-carboxamide fumarate, N-(pyridazin-3-yl)-2-(2,2,6,6-tetramethylmorpholin-4-yl)-5,6,8,9-tetrahydrooxepino[4,5-b]pyridine-4-carboxamide hydrochloride, 2-[(2R,6S)-2,6-dimethylmorpholin-4-yl]-N-(5-fluoropyridin-2-yl)-5,6,8,9-tetrahydrooxepino[4,5-b]pyridine-4-carboxamide, N-(5-chloropyridin-2-yl)-2-[(2R,6S)-2,6-dimethylmorpholin-4-yl]-5,6,8,9-tetrahydrooxepino[4,5-b]pyridine-4-carboxamide hydrochloride, N-(5-chloropyridin-2-yl)-2-[(2R,6S)-2,6-dimethylmorpholin-4-yl]-5,6,8,9-tetrahydrooxepino[4,5-b]pyridine-4-carboxamide p-toluenesulfonate, N-(5-chloropyridin-2-yl)-2-[(2R,6S)-2,6-dimethylmorpholin-4-yl]-5,6,8,9-tetrahydrooxepino[4,5-b]pyridine-4-carboxamide benzenesulfonate, N-(6-methoxypyridazin-3-yl)-2-[(2R)-2-methylpyrrolidin-1-yl]-5,6,8,9-tetrahydrooxepino[4,5-b]pyridine-4-carboxamide phosphate, N-(6-methylpyrazin-2-yl)-2-[(2S)-2-methylpyrrolidin-1-yl]-5,6,8,9-tetrahydrooxepino[4,5-b]pyridine-4-carboxamide hydrochloride, 2-[(2R)-2-ethylmorpholin-4-yl]-N-(6-methylpyridin-3-yl)-5,6,8,9-tetrahydrooxepino[4,5-b]pyridine-4-carboxamide hydrochloride, N-(5,6-dimethylpyrazin-2-yl)-2-[(2R)-2-methylpyrrolidin-1-yl]-5,6,8,9-tetrahydrooxepino[4,5-b]pyridine-4-carboxamide hydrochloride, N-(3-cyanophenyl)-2-[(3S)-3-methoxypyrrolidin-1-yl]-5,6,8,9-tetrahydrooxepino[4,5-b]pyridine-4-carboxamide hydrochloride, 2-(4-fluoropiperidin-1-yl)-N-(pyridazin-3-yl)-5,6,8,9-tetrahydrooxepino[4,5-b]pyridine-4-carboxamide hydrochloride, N-(5-chloropyridin-2-yl)-2-(4-fluoropiperidin-1-yl)-5,6,8,9-tetrahydrooxepino[4,5-b]pyridine-4-carboxamide, N-(5,6-dimethylpyrazin-2-yl)-2-[(2S)-2-methylpyrrolidin-1-yl]-5,6,8,9-tetrahydrooxepino[4,5-b]pyridine-4-carboxamide hydrochloride, 2-[(2S)-2-methylpiperidin-1-yl]-N-(pyridazin-3-yl)-5,6,8,9-tetrahydrooxepino[4,5-b]pyridine-4-carboxamide hydrochloride, 2-[(2S)-2-methylpiperidin-1-yl]-N-(pyrazin-2-yl)-5,6,8,9-tetrahydrooxepino[4,5-b]pyridine-4-carboxamide hydrochloride, and N-(5-chloropyridin-2-yl)-2-[(3S)-3-fluoropiperidin-1-yl]-5,6,8,9-tetrahydrooxepino[4,5-b]pyridine-4-carboxamide benzenesulfonate.

The compound of the formula (I) may exist in the form of tautomers or geometrical isomers depending on the kind of substituents. In the present specification, the compound of the formula (I) may be described in only one form of isomers, yet the present invention includes any other isomers, isolated forms of the isomers, or a mixture thereof.

In addition, the compound of the formula (I) may have asymmetric carbon atoms or axis chirality in some cases, and correspondingly, it may exist in the form of optical isomers. The present invention also includes an isolated form of the optical isomers of the compound of the formula (I) or a mixture thereof.

Further, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in, for example, Progress in Medicine, 1985, vol. 5, 2157-2161 and "Pharmaceutical Research and Development" (Hirokawa-Shoten Ltd.) 1990, Vol. 7 (Molecular Design) pp. 163 to 198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, and phosphoric acid; and acid addition salts with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid (besylic acid), p-toluenesulfonic acid (4-methylbenzenesulfonic acid, tosic acid), aspartic acid, and glutamic acid.

The present invention further includes various hydrates or solvates, and polymorphic crystal substances of a compound of the formula (I) and a salt thereof. In addition, the present invention also includes compounds labeled with various radioactive or non-radioactive isotopes.

As used herein, the term "CIAS" refers to cognitive impairment associated with schizophrenia.

The "negative symptoms of schizophrenia" refers to negative symptoms in schizophrenia.

(Preparation Methods)

The compound of the formula (I) and a salt thereof can be prepared using the characteristics based on the basic structure or the type of substituent thereof and by using various known synthesis methods. During the preparation, replacing the relevant functional group with a suitable protective group (a group that can be easily converted into the relevant functional group) at the stage of starting materials or intermediates may be effective depending on the type of the functional group in the production in some cases. Examples of such a protective group include those described in by Peter G M. Wuts and Theodora W. Greene, "Greene's Protective Groups in Organic Synthesis ($4^{th}$ edition), 2006", and the like, and one of these may be appropriately selected depending on reaction conditions. A desired compound can be obtained by introducing the protective group to carry out a reaction, and then by eliminating the protective group as necessary.

In addition, the prodrug of the compound of the formula (I) can be prepared by introducing a specific group at the stage from a starting material to an intermediate or by further carrying out the reaction using the obtained compound of the formula (I), just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the preparation methods may also be carried out with reference to the References. Further, the preparation methods of the present invention are not limited to the examples as shown below.

The following abbreviations may be used in some cases in the present specification.

AcOEt: ethyl acetate, AcCl: acetyl chloride, brine: saturated brine, BINAP: 1,1'-binaphthalene-2,2'-diylbis (diphenylphosphine), nBuLi: n-butyllithium, tBuOH: tert-butyl alcohol, Comins reagent: N-(5-chloro-2-pyridyl)triflimide, DIPEA: N,N-diisopropylethylamine, DMAP: N,N-dimethyl-4-aminopyridine, DME: dimethoxyethane, DMF: N,N-dimethylformamide, DMSO: dimethylsulfoxide, dppf: 1,1'-bis(diphenylphosphino)ferrocene, EtOH: ethanol, Et$_2$O: diethyl ether, Et$_3$N: triethylamine, FM: fumaric acid, Ghosez reagent: 1-chloro-N,N,2-trimethyl-1-propenyl amine, Grubbs catalyst: benzylidene[1,3-bis(2,4,6-trimethylphenyl)-2-imidazolidinylidene]dichloro(tricyclohexylphosphine)ruthenium, HATU: 1-[bis(dimethylamino)methylene]-1H-1,2,3-triazolo[4,5-b]pyridinium 3-oxide hexafluorophosphate, HOBt: 1-hydroxybenzotriazole, iPr$_2$O: diisopropyl ether, iPrOH: 2-propanol, KHMDS: potassium hexamethyldisilazide, KOtBu: potassium tert-butoxide, LDA: lithium diisopropylamide, LHMDS: lithium hexamethyldisilazide, LiTMP: lithium 2,2,6,6-tetramethylpiperidide, McMurry's reagent: 1,1,1-trifluoro-N-phenyl-N-[(trifluoromethyl)sulfonyl]methanesulfonamide, MeCN: acetonitrile, MeOH: methanol, MgSO$_4$: anhydrous magnesium sulfate, NBS: N-bromosuccinimide, NMP: N-methyl-2-pyrrolidone, NaHMDS: sodium hexamethyldisilazide, Na$_2$SO$_4$: anhydrous sodium sulfate, NaOtBu: sodium tert-butoxide, OsO$_4$—NaIO$_4$: osmium tetroxide-sodium periodate, Pd(OAc)$_2$: palladium acetate (II), Pd(dba)$_2$: bis(dibenzylideneacetone)palladium (0), Pd$_2$(dba)$_3$: tris (dibenzylideneacetone)palladium (0), Pd(PPh$_3$)$_4$: tetrakis (triphenylphosphine)palladium (0), Pd/C: palladium on carbon, Pd(OH)$_2$/C: palladium hydroxide on carbon, Pt/C: platinum on carbon, PyCLU: 1-(chloro-1-pyrrolidyl methylene)pyrrolidinium hexafluorophosphate, TBAF: tetra-n-butylammonium fluoride, TBAI: tetrabutylammonium iodide, TCFH: chloro-N,N,N',N'-tetramethyl formamidinium hexafluorophosphate, TFFH: fluoro-N,N,N',N'-tetramethyl-formamidinium hexafluorophosphate, THF: tetrahydrofuran, Tf$_2$O: (CF$_3$SO$_2$)$_2$O, Wilkinson complex: chlorotris(triphenylphosphine)rhodium (I), WSC hydrochloride: N-[3-(dimethylamino)propyl]-N'-ethylcarbodiimide hydrochloride, tBu$_2$BINAP: 1,1'-binaphthalen-2-yl(di-tertbutyl) phosphine, silica gel CC: silica gel column chromatography.

In this specification, in particular the chemical structural formula, the following abbreviations may be used in some cases.

Ac: CH$_3$C(=O), BOC: tert-butoxycarbonyl, Et: C$_2$H$_5$, Me: CH$_3$, OMe: OCH$_3$, Tf: CF$_3$SO$_2$, PMB: p-methoxybenzyl.

(First Preparation Method)

[Chem. 10]

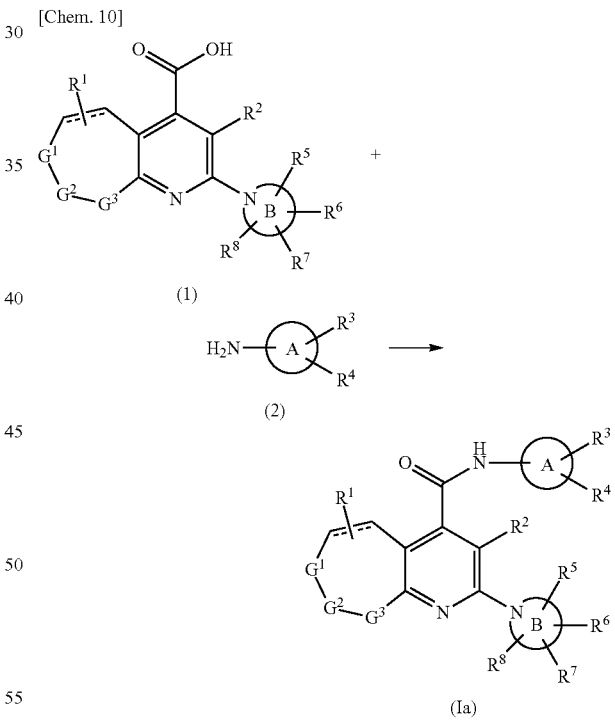

(In the formula, ==== represents a single bond or a double bond. The same shall apply hereinafter).

(The compound (I) of the present invention is a compound wherein ==== in the compound (Ia) is a single bond).

[1] The compound (Ia) can be prepared by amidation of the compound (1) and the compound (2). This reaction can be carried out by preparing an acid halide as an intermediate from carboxylic acid and a halogenating reagent in a solvent inert to the reaction and adding a base and an amine thereto. Further, depending on the substrate, an acid halide may be isolated once. The solvents that can be used are aromatic hydrocarbons such as toluene and the like, halogenated hydrocarbons such as CH$_2$Cl$_2$, CHCl$_3$, and the like, ethers such as Et$_2$O, THF, and the like, DMF, DMSO, AcOEt, MeCN, water, and mixed solvents thereof. The halogenating reagents that can be used are a Ghosez reagent, PyCLU, TCFH, TFFH, SOCl$_2$, POCl$_3$, and the like. Additionally, this reaction may be carried out by adding a small amount of DMF to SOCl$_2$. The base that can be used is an organic base such as pyridine and the like.

The activated intermediate of the carboxy group may be mixed acid anhydride or active ester, or the like, in addition to the above-mentioned acid halide.

As another preparation method, a method using a condensing agent may be used. This reaction can be carried out in a solvent inert to the reaction by adding a condensing agent and a base. The condensing agent that can be used is WSC hydrochloride, HATU, or the like. The solvent that can be used is halogenated hydrocarbons, NMP, or the like. The base that can be used is an organic base such as pyridine, Et$_3$N, DIPEA, DMAP, or the like, or an inorganic base such as K$_2$CO$_3$, Na$_2$CO$_3$, KOH, or the like. The reaction may proceed smoothly in some cases with the addition of HOBt or the like during the reaction.

[Literature] "Organic Syntheses", 1980, vol. 59, p. 26.

[2] The compound (I) of the present invention can also be prepared by hydrogenation of a compound wherein ---- in the compound (Ia) is a double bond. Further, the reduction may be carried out at a stage that does not affect other functional groups in any step from a starting material to a desired product, or a compound wherein ---- is a single bond can be used from starting materials. The hydrogenation can be carried out under a hydrogen atmosphere in a solvent inert to the reaction in the presence of a metal catalyst. The solvent that can be used is alcohols such as MeOH, or the like. The metal catalyst that can be used include a palladium catalyst such as Pd/C, Pd(OH)$_2$/C, or the like, a platinum catalyst such as Pt/C or the like, a nickel catalyst such as Raney nickel or the like, a rhodium catalyst such as Wilkinson complex or the like, and an iron catalyst such as reduced iron or the like. As a hydrogen source, formic acid or ammonium formate may be used in place of hydrogen gas.

[Literature] "Reductions in Organic Chemistry", 2nd edition, ACS Monograph: 188, ACS, 1996; and "Courses in Experimental Chemistry (5$^{th}$ edition)", Volume 19 (2005), edited by The Chemical Society of Japan (Maruzen Publishing Co. Ltd.)

(Second Preparation Method)

[Chem. 11]

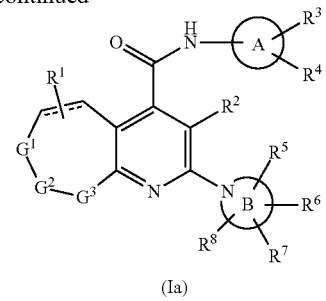

(3)

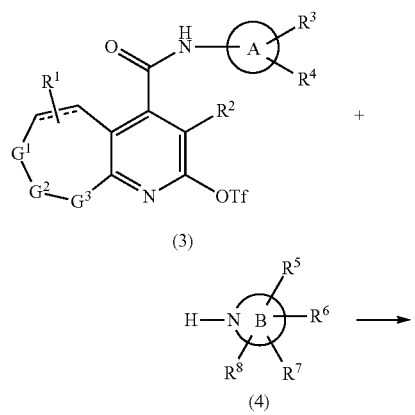

(4)

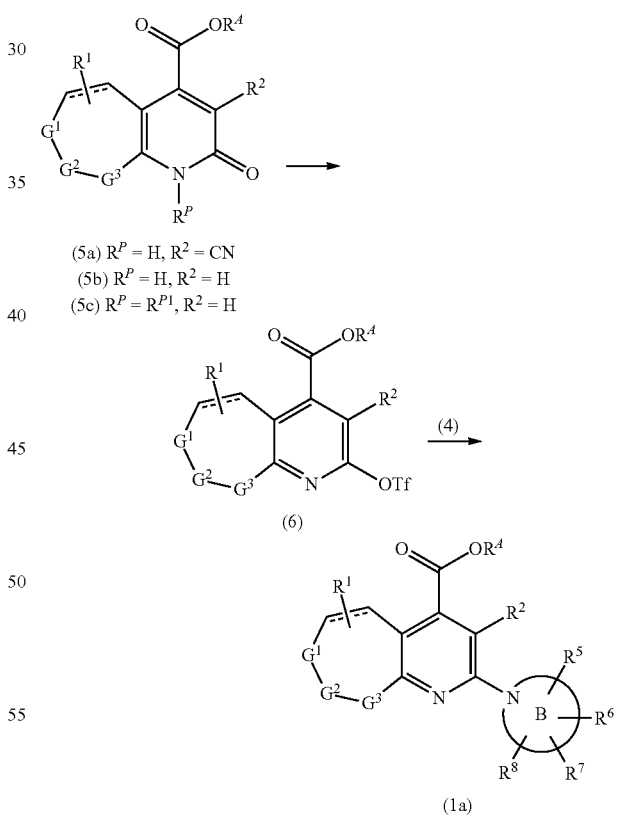

(Ia)

The compound (Ia) can be prepared from the compound (3) and the compound (4). This reaction can be carried out in a solvent inert to the reaction or without a solvent at room temperature to under heating to reflux. The solvent that can be used is aromatic hydrocarbons, ethers, halogenated hydrocarbons, alcohols such as EtOH or the like, DMF, DMSO, AcOEt, MeCN, NMP, water, and mixed solvents thereof. Further, the reaction may proceed smoothly in some cases by the addition of an organic base or an inorganic base during the reaction.

(Starting Material Preparation Method 1)

[Chem. 12]

(5a) R$^P$ = H, R$^2$ = CN
(5b) R$^P$ = H, R$^2$ = H
(5c) R$^P$ = R$^{P1}$, R$^2$ = H (In the formula, R$^A$ represents a protecting group of the carboxy group. R$^P$ represents H or R$^{P1}$, and R$^{P1}$ represents a protecting group of the amide group. The same shall apply hereinafter).

The compound (1a) can be prepared using the compound (5a), (5b) or (5c) as a starting material. R$^{P1}$ is, for example, a PMB group or the like. The compound (6) can be prepared by triflation of the compound (5a), (5b) or (5c). An example of $R^A$ is lower alkyl or the like, and an example of $R^{P1}$ is PMB or the like. This reaction can be carried out in a halogenated hydrocarbon solvent such as $CH_2Cl_2$ or the like using a triflating reagent, an inorganic base or an organic base such as pyridine or the like. The triflating reagent that can be used is $Tf_2O$, McMurry's reagent, a Comins reagent, or the like. The compound (1a) can be prepared from the compound (6) and the compound (4). This reaction may employ the conditions of the above-mentioned second preparation method.

The compound (1) can be prepared by deprotecting the compound (1a). This reaction can be carried out in a solvent inert to the reaction or without a solvent at room temperature to under heating to reflux. The solvent that can be used is aromatic hydrocarbons, ethers, halogenated hydrocarbons, alcohols such as EtOH or the like, DMF, DMSO, AcOEt, MeCN, NMP, water, and mixed solvents thereof. The reaction may proceed smoothly in some cases by adding an organic base or an inorganic base during the reaction.

Further, in preparing the compound (1a) from the compound (5a), (5b) or (5c), the compound (1a) may also be prepared without isolation of the compound (6) depending on the substrate.

(Starting Material Preparation Method 2)

[Chem. 13]

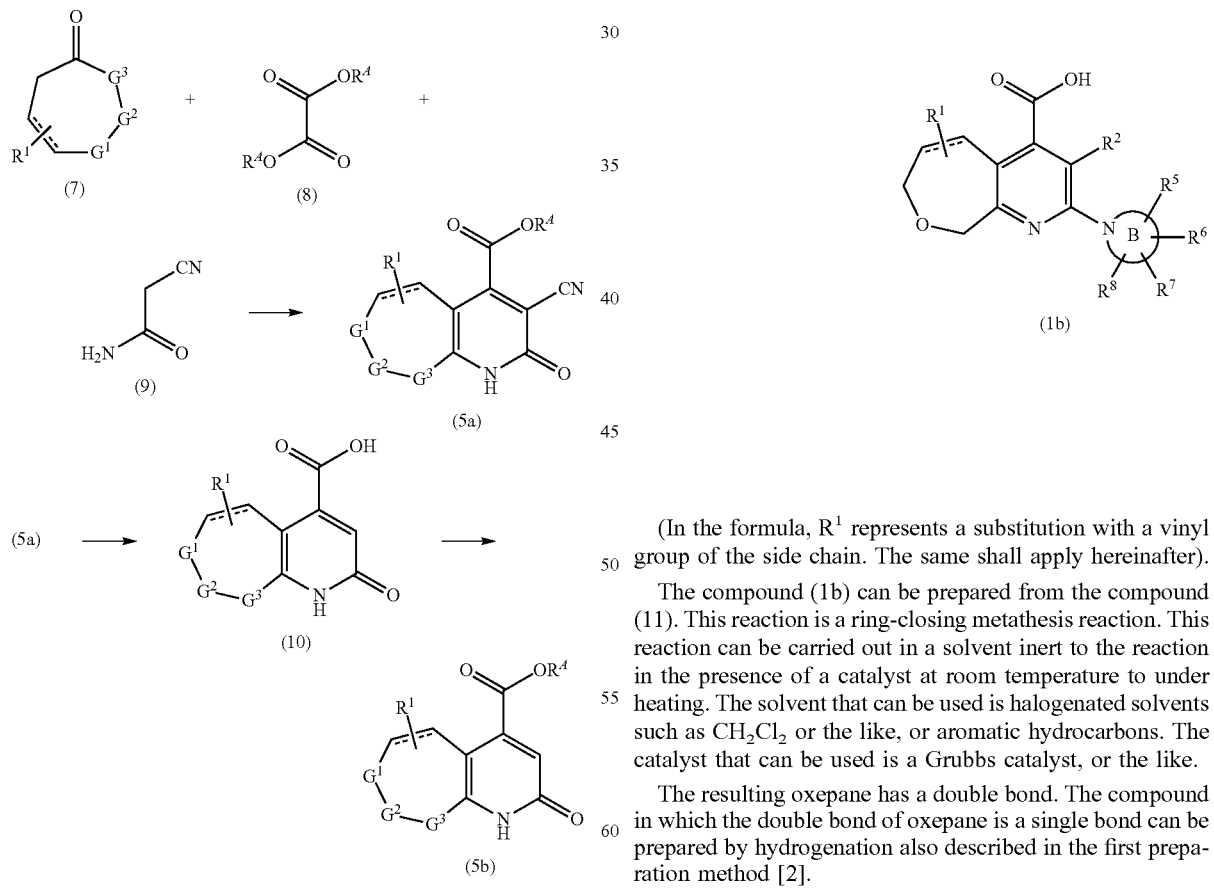

The compound (5b) can be prepared using the compound (7) as a starting material. The compound (5a) can be prepared from the compound (7), the compound (8) and the compound (9). This reaction can be carried out in a solvent inert to the reaction in the presence of a base under heating. The solvent that can be used is alcohols such as EtOH or the like. The base that can be used is an inorganic base such as KOtBu or the like. The compound (5b) can be prepared via the compound (10) from the compound (5a). The compound (10) can be prepared from the compound (5a). This reaction proceeds with simultaneous occurrence of CN group elimination and deprotection. This reaction can be carried out in a concentrated hydrochloric acid under heating. The compound (5b) can be prepared by re-protecting the carboxy group of the compound (10).

(Starting Material Preparation Method 3)

[Chem. 14]

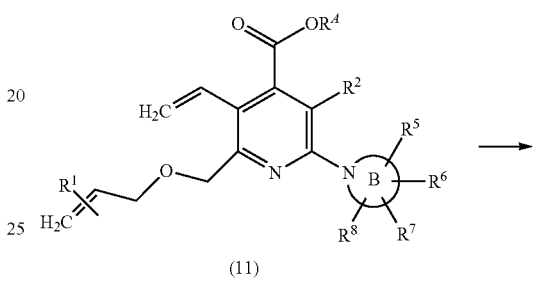

(In the formula, $R^1$ represents a substitution with a vinyl group of the side chain. The same shall apply hereinafter).

The compound (1b) can be prepared from the compound (11). This reaction is a ring-closing metathesis reaction. This reaction can be carried out in a solvent inert to the reaction in the presence of a catalyst at room temperature to under heating. The solvent that can be used is halogenated solvents such as $CH_2Cl_2$ or the like, or aromatic hydrocarbons. The catalyst that can be used is a Grubbs catalyst, or the like.

The resulting oxepane has a double bond. The compound in which the double bond of oxepane is a single bond can be prepared by hydrogenation also described in the first preparation method [2].

[Literature] "Angewandte Chemie International Edition", 2006, vol. 45, pp. 3760 to 3765; and "Courses in Experimental Chemistry ($5^{th}$ edition)", Volume 19 (2005), edited by The Chemical Society of Japan (Maruzen Publishing Co. Ltd.)

(Starting Material Preparation Method 4)

[Chem. 15]

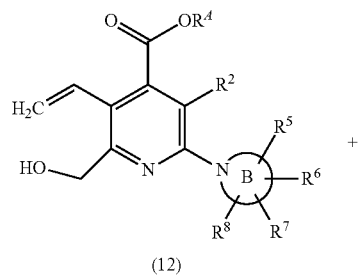

(12)

+

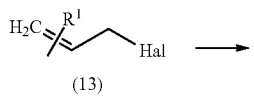

(13)

→

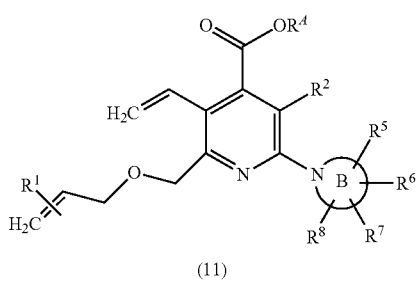

(11)

(In the formula, Hal is halogen. The same shall apply hereinafter).

The compound (11) can be prepared from the compound (12) and the compound (13). The reaction can be carried out in a solvent inert to the reaction in the presence of a base at room temperature to under heating to reflux. The solvent that can be used is aromatic hydrocarbons, ethers, halogenated hydrocarbons, DMF, DMSO, AcOEt, MeCN and mixed solvents thereof. The base that can be used is an organic base, an inorganic base such NaH, or the like. The reaction may proceed smoothly in some cases by a phase transfer catalyst such as TBAI or the like.

(Starting Material Preparation Method 5)

[Chem. 16]

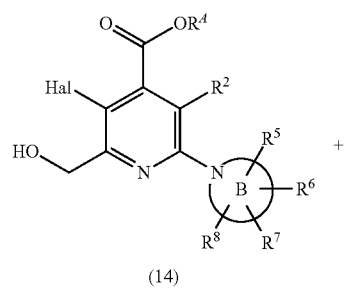

(14)

+

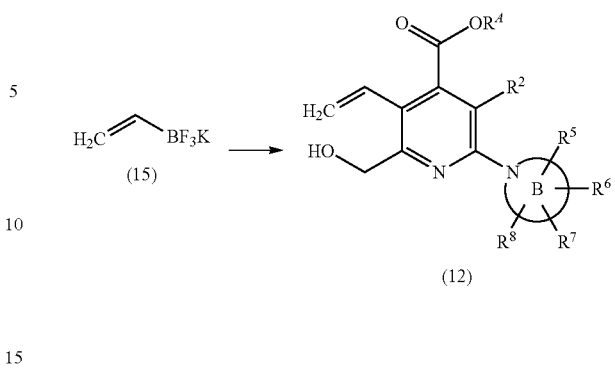

(12)

The compound (12) can be prepared from the compound (14) and the compound (15). This reaction can be carried out in a solvent inert to the reaction in the presence of a palladium catalyst and a base under heating. The solvent that can be used is a mixed solvent of an organic solvent and water, for example, THF—$H_2O$, dioxane-$H_2O$, toluene-EtOH—$H_2O$, DME-$H_2O$, or the like. The palladium catalyst that can be used is $Pd(PPh_3)_4$ or the like. The inorganic base that can be used is KF, CsF or $NaHCO_3$. The organic base that can be used is $Et_3N$ or the like.

[Literature] "Journal of Organic Chemistry", 2006, vol. 71(26), pp. 9681 to 9686; and ibid., 2009, vol. 74(6), pp. 2321 to 2327.

(Starting Material Preparation Method 6)

[Chem. 17]

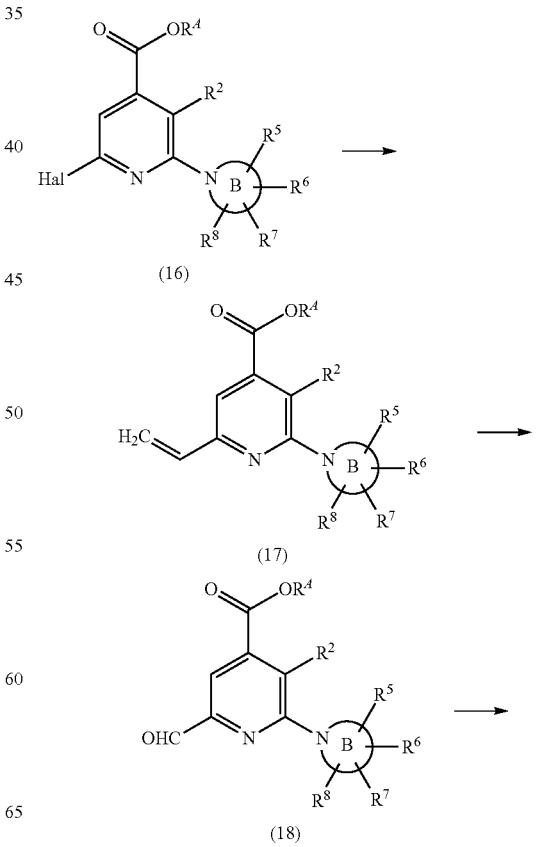

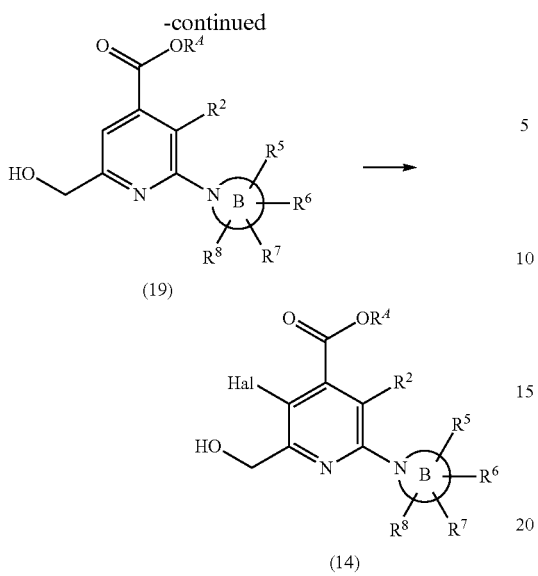

(19)

(14)

The compound (14) can be prepared using the compound (16) as a starting material. The compound (17) can be prepared from the compound (16) and the compound (15) described above. The same conditions as in Starting material preparation method 5 can be used. The compound (18) can be prepared from the compound (17). This reaction is oxidative cleavage using an oxidizing agent such as OsO$_4$—NaIO$_4$ or the like and may employ conventional conditions. The compound (19) can be prepared from the compound (18). This reaction is reduction and may employ NaBH$_4$ or the like as a reducing agent. The compound (14) can be prepared from the compound (19). This reaction is halogenation. This reaction may employ a halogenating agent such as N-halosuccinimide or the like as a reagent.

(Starting Material Preparation Method 7)

[Chem. 18]

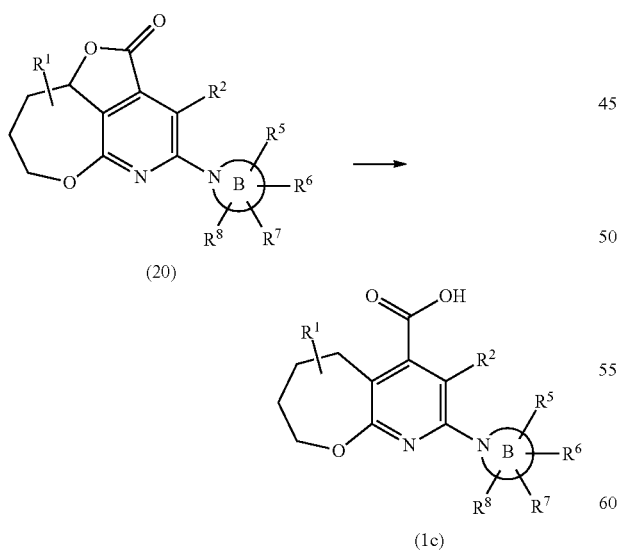

(20)

(1c)

The compound (1c) can be prepared from the compound (20). This reaction is hydrogenation. This reaction may employ the conditions described in the first preparation method [2].

(Starting Material Preparation Method 8)

[Chem. 19]

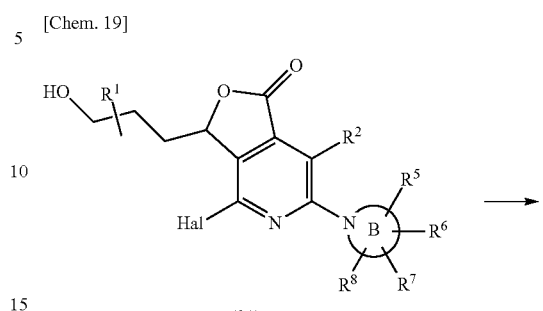

(21)

(20)

The compound (20) can be prepared from the compound (21). This reaction is ether synthesis of so-called Buchwald-Hartwig cross-coupling. This reaction can be carried out in a solvent inert to the reaction in the presence of a base, a palladium catalyst and a phosphine ligand at room temperature. The solvent that can be used is aromatic hydrocarbons such as toluene or the like. The palladium catalyst that can be used is Pd(OAc)$_2$, Pd(dba)$_2$, or the like. The base that can be used is an inorganic base such as Cs$_2$CO$_3$, NaOtBu, or the like. The phosphine ligand that can be used is tBu$_2$BINAP, ferrocenyl phosphine, or the like.

[Literature] "Angewandte Chemie International Edition", 1998, vol. 37, pp. 2046 to 2067

(Starting Material Preparation Method 9)

[Chem. 20]

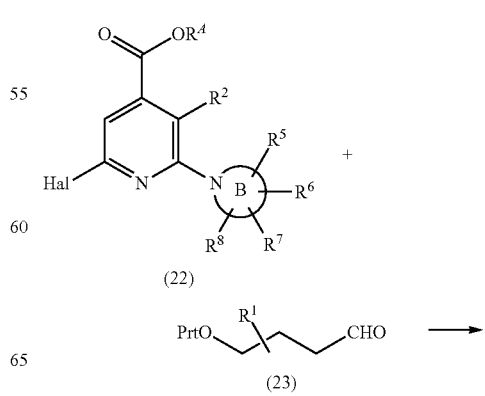

(22)

(23)

-continued

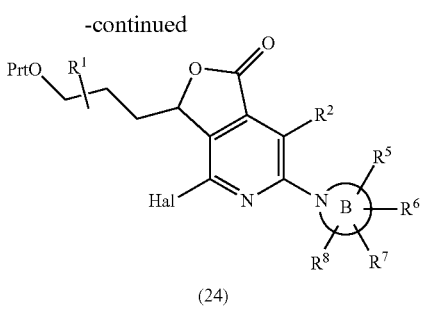

(24)

(In the formula, Prt is a protecting group)

The compound (24) can be prepared from the compound (22) and the compound (23). Prt is, for example, a tert-butyl (dimethyl)silyl group or the like. This reaction can be carried out in a solvent inert to the reaction in the presence of a base. The base that can be used is a lithium amide-based reagent such as LDA, LiTMP, LHMDS, or the like. The compound (21) can be prepared by deprotection of the compound (24).

(Starting Material Preparation Method 10)

[Chem. 21]

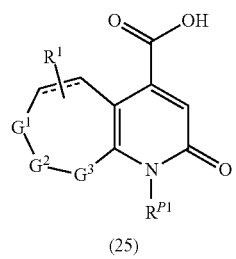

(25)

+

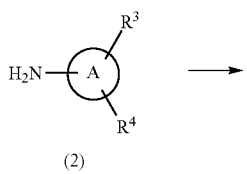

(2)

→

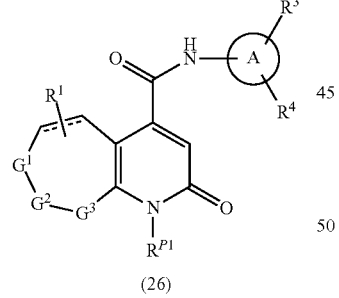

(26)

(26) →

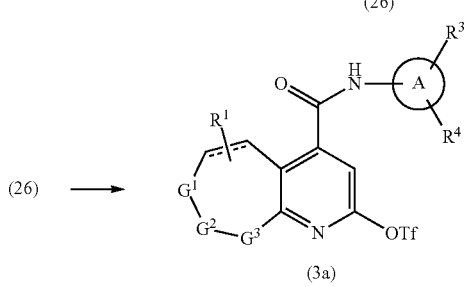

(3a)

The compound (3a) can be prepared using the compound (25) as a starting material. The compound (26) can be prepared from the compound (25) and the compound (2).

This reaction is amidation and may employ the conditions described in the first preparation method [1]. The compound (3a) can be prepared from the compound (26). This reaction is triflation and may employ the conditions described in the Starting material preparation method 1.

(Starting Material Preparation Method 11)

[Chem. 22]

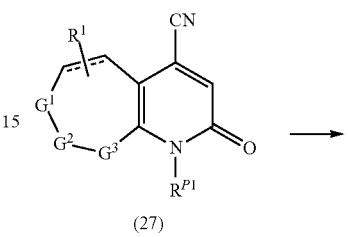

(27)

→

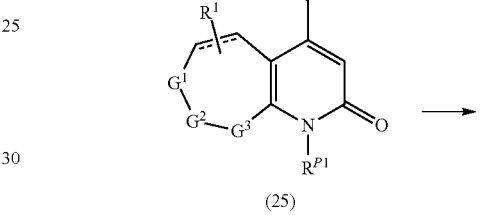

(25)

→

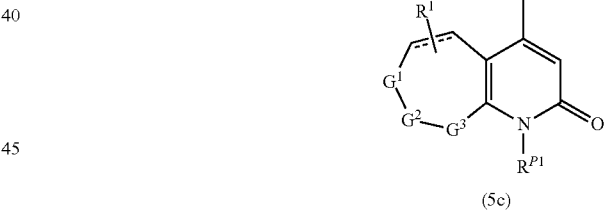

(5c)

The compound (5c) can be prepared using the compound (27) as a starting material. The compound (25) can be prepared by hydrolysis of the compound (27). This reaction can be carried out in a solvent inert to the reaction in the presence of a base at room temperature to under heating for several hours to overnight. The solvent that can be used is an alcohol. The base that can be used is an aqueous NaOH solution or the like.

The compound (5c) can be prepared from the compound (25). This reaction can be generally carried out in a solvent inert to the reaction in the presence of halogenated alkyl and a base at room temperature to under heating for several hours to overnight. The solvent that can be used is MeCN or the like. The halogenated alkyl is $R^4X$ (X is a leaving group such as Cl, Br, I, or the like), and an example of $R^4$ is methyl. The base that can be used is an inorganic base such as $K_2CO_3$ or the like.

(Starting Material Preparation Method 12)

[Chem. 23]

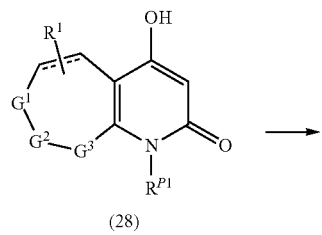
(28)

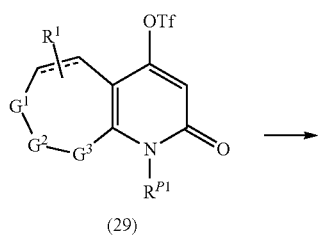
(29)

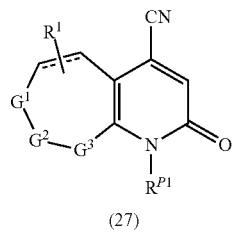
(27)

The compound (27) can be prepared using the compound (28) as a starting material. The compound (29) can be prepared from the compound (28). This reaction can be carried out in the same manner as in the above-mentioned Starting material preparation method 1. The compound (27) can be prepared from the compound (29). This reaction can be carried out in a solvent inert to the reaction in the presence of a CN source, a palladium catalyst, a phosphine ligand, $CH_3SO_2Na$ and the like under heating for several hours to overnight. The solvent that can be use is DMF, $H_2O$, or the like. CN source that can be use is NaCN, KCN, $Zn(CN)_2$, or the like. The palladium catalyst that can be use is $Pd_2(dba)_3$, or the like. The phosphine ligand that can be used is dppf, or the like.

(Starting Material Preparation Method 13)

[Chem. 24]

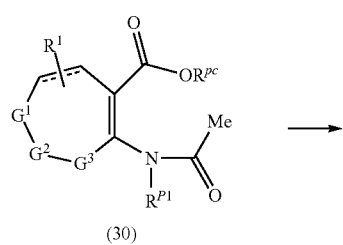
(30)

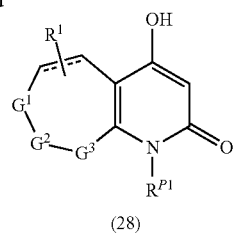
(28)

The compound (28) can be prepared from the compound (30). This reaction can be carried out for several hours to several days by adding a lithium amide reagent to the compound (30) at −30° C. to −80° C., followed by elevating the temperature. The solvent that can be used is THF, toluene, or the like. The lithium amide reagent that can be used is LDA, LiTMP, LHMDS, KHMDS, or NaHMDS.

(Starting Material Preparation Method 14)

[Chem. 25]

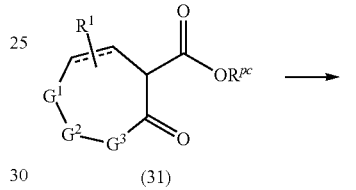
(31)

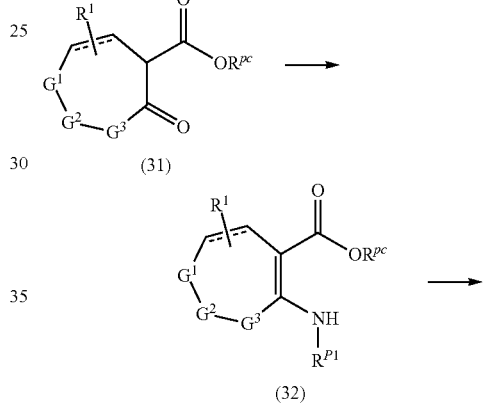
(32)

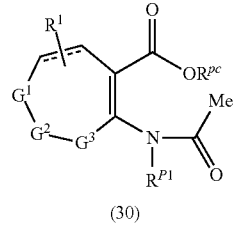
(30)

The compound (30) can be prepared using the compound (31) as a starting material. The compound (32) can be prepared from the compound (31). This reaction can be carried out in a solvent inert to the reaction in the presence of $R^{P1}$—$NH_2$ and an acid at room temperature to under heating for one hour to several hours. The solvent that can be used is alcohols such as EtOH or the like. The acid that can be used is acetic acid. The compound (30) can be prepared by acylation of the compound (32). This reaction can be carried out in a solvent inert to the reaction under heating for several hours after adding MeC(=O)X (X is a leaving group such as Cl, Br, I, or the like) under ice-cooling. The solvent that can be used is THF or the like.

The compound of the formula (I) is isolated and purified as a free compound, a salt, a hydrate, a solvate, or a polymorphic crystal substance thereof. A salt of the compound of the formula (I) can be prepared by carrying out a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or can be separated by using the difference in the physicochemical properties between the isomers. For example, the optical isomers can be obtained by means of a general method for designing optical resolution of racemic compounds (for example, fractional crystallization for inducing diastereomer salts with optically active bases or acids, chromatography using a chiral column or the like, and others), and further, the isomers can also be prepared from an appropriate optically active starting compound.

Furthermore, for the sake of convenience, a concentration mol/L is expressed as M. For example, a 1 M aqueous NaOH solution means a 1 mol/L aqueous NaOH solution.

The pharmacological activity of the compound of the formula (I) was confirmed by the following tests.

(Abbreviation)

In the following Test Examples of the present specification, the following abbreviations may be used in some cases.

AChCl: Acetylcholine chloride, ATCC: American Type Culture Collection, DMEM: Dulbecco's modified Eagle's medium, EGTA: Ethylene glycol-bis(2-aminoethylether)-N,N,N',N'-tetraacetic acid, FBS: Fetal bovine serum, HBSS: Hank's Balanced Salt Solution, HEK293 cells: Human embryonic kidney cells, HEPES: 4-(2-hydroxyethyl)-1-piperazineethanesulfonic acid, NMDA:N-methyl-D-aspartate, PNU-120596: 1-(5-chloro-2,4-dimethoxyphenyl)-3-(5-methyl-1,2-oxazol-3-yl)urea (CAS registry number:501925-31-1). PNU-282987: N-(3R)-1-azabicyclo[2.2.2]octo-3-yl-4-chlorobenz amide (CAS registry number: 123464-89-1).

(Materials)

The composition of the buffer used in Test Example 1 is shown.

Assay buffer: HBSS buffer containing 1.25 mM probenecid.

Test Example 1 Evaluation for Human α7 nACh Receptor Using FLIPR

The PAM activity of a test drug was evaluated in terms of $Ca^{2+}$ dye-based fluorescence intensity for an intracellular calcium response in the presence of an α7 nACh receptor-selective agonist PNU-282987 (CAS registry number: 123464-89-1, Tocris) using a FLIPR tetra (Molecular Devices).

In the case where a concentration-response curve has been obtained in which the logarithm of a concentration of a test drug is on the abscissa and the ratio of a response (hereinafter, also referred to as calcium response) is on the ordinate, this test drug has been determined to have a PAM activity.

In this test, the agonist (PNU-282987) elicited a calcium response only in the presence of PAM (PNU-120596).

(Acquisition of Cells Transiently Co-Expressing Human α7 nACh Receptor/RIC3)

The coding sequence of a human α7 nACh receptor (accession number: NM_000746.5) was subcloned into a pCEP4 vector (Life Technologies). The coding sequence of a rat chaperone protein RIC3 (accession number: NM_001115045.3) was subcloned into a pcDNA3.1/Hygro (+) vector (Life Technologies). The resulting constructs were transfected into HEK293 cells (ATCC number: CRL-1573) by an electroporation method using Neon (Life Technologies).

(Test Method)

Concentration-Response Curve of Human α7 nACh Receptor with Addition of Test Drug The concentration-response curve of a human α7 nACh receptor with the addition of a test drug was produced by the following experiment.

The transiently expressing cells obtained in the manner described above were seeded at a density of $8 \times 10^3$ cells/well onto a 384-well plate (Becton Dickinson) and allowed to stand overnight at 37° C. DMEM+10% FBS was used as a medium.

On the next day, the medium was removed, and Fluo4-AM (Dojindo) prepared using an assay buffer was applied, followed by allowing to stand for 1 hour. The test drug was dissolved in DMSO and then made to a final concentration of 0.03 to 100 µM (3-fold dilutions) with an assay buffer. Similarly, PNU-120596 which is a known PAM was made to a final concentration of 0.003 to 10 µM (3-fold dilutions). PNU-282987 which is an agonist was made to a final concentration of 0.6 µM. Thereafter, the test drug was applied to the cells using a FLIPR tetra, the agonist (PNU-282987) was added 5 minutes later, and the fluorescence intensity at that time was detected.

As a control, using (1) a group with neither addition of a test drug, PAM (PNU-120596) nor that of agonist (PNU-282987), the response thereof was set to 0%. Using (2) a group with the addition of PAM (PNU-120596) and agonist (PNU-282987), the maximum response thereof was set to 100%.

(Evaluation of Activity)

As a result of the tests above, some representative Example compounds of the present invention exhibited an enhanced concentration-dependent response (calcium response) when those compounds were added in the presence of an agonist (PNU-282987), and the concentration-response curve of the human α7 nACh receptor was obtained. Further, the calcium response was not elicited with an agonist (PNU-282987) alone, or some representative Example compounds of the present invention alone. From the foregoing results, it was demonstrated that compounds of the present invention have a PAM activity on a human α7 nACh receptor.

To quantitatively compare the PAM activity of the test drug, an $EC_{20}$ value and a Max value were used as activity indicators. The $EC_{20}$ value refers to a test drug concentration exhibiting the response intensity of 20%, in the concentration-response curve, when setting the maximum response of PAM (PNU-120596) in the presence of an agonist (PNU-282987) to 100%. The $EC_{20}$ value was calculated using a non-linear regression analysis from the concentration-response curve of a human α7 nACh receptor with the addition of a test drug. The Max value refers to a maximum response value. The Max value is expressed in terms of % value of the maximum response of a test drug in the presence of an agonist (PNU-282987) relative to when the maximum response of PAM (PNU-120596) in the presence of an agonist (PNU-282987) is set to 100%.

The results of some representative Example compounds of the present invention ($EC_{20}$ value and Max value) are shown in Table below. In the Table, No. represents a Compound No., and Ex represents an Example Compound No.

TABLE 1

| No. | EC$_{20}$ (µM) | Max (%) |
|---|---|---|
| Ex 1 | 2.72 | 99.8 |
| Ex 7 | 0.512 | 94.8 |
| Ex 9 | 3.52 | 69.3 |
| Ex 12 | 4.35 | 96.9 |
| Ex 18 | 1.02 | 79.2 |

Test Example 2 Electrophysiological Evaluation for Human α7 nACh Receptor

The PAM activity of a test drug was evaluated by a current response in the presence of an α7 nACh receptor agonist Acetylcholine chloride (Sigma) (hereinafter, also referred to as AChCl) using Qpatch HTX (Biolin Scientific) or Qube (Biolin Scientific). This test cannot detect a small current response of AChCl alone. The current response can be detected only in the case where the test drug has a PAM activity.

(Materials)

The composition of extracellular fluid and intracellular fluid used in Test Example 2 is shown below.

Extracellular fluid (pH 7.4): NaCl 145 mM, KCl 4 mM, HEPES 10 mM, CaCl$_2$ 2 mM, MgCl$_2$ 1 mM.

Intracellular fluid (pH 7.2): KF 120 mM, KCl 20 mM, EGTA 0.1 mM, HEPES 10 mM, MgCl$_2$ 2 mM.

(Acquisition of Cells Transiently Co-Expressing Human α7 nACh Receptor/RIC3)

The cells were obtained in the same manner as in Test Example 1.

(Test Method)

Response of Human α7 nACh Receptor with Addition of Test Drug

The response of a human α7 nACh receptor with the addition of a test drug was measured by the following experiment. Transient expression cells obtained by the method described above were subjected to the experiment after allowing to stand overnight at 37° C. The test drug was dissolved in DMSO, and then made to a final concentration of 3 µM using extracellular fluid. The agonist AChCl was made to a final concentration of 100 µM. The membrane potential was voltage-clamped at −90 mV. The current response was measured by multi-hole mode at the time of simultaneous addition of the test drug and AChCl to the cells, using QPatch HTX or Qube.

(Evaluation of Activity)

As a result of the tests above, the case where an inward current response specific to a human α7 nACh receptor was obtained when 3 µM of a test drug had been added was determined as positive, and the case where a specific current response was not observed was determined as negative. It should be noted that, when the agonist concentration is 0, the current response was not observed even with the addition of a test drug.

The results of some representative Example compounds of the present invention are shown in Table below. In the Table, No. represents a Compound No., Ex represents an Example Compound No., and Dat.1 represents Determination.

TABLE 2

| No. | Dat. 1 |
|---|---|
| Ex 18 | positive |
| Ex 36 | positive |
| Ex 40 | positive |
| Ex 46 | positive |
| Ex 48 | positive |
| Ex 50 | positive |
| Ex 51 | positive |
| Ex 55 | positive |
| Ex 69 | positive |
| Ex 70 | positive |
| Ex 76 | positive |

Test Example 3 Y-Maze Test

The improving effect of the compound of the present invention on cognitive impairment was evaluated using a Y-maze test which is an experimental system of spontaneous alternation behavior.

(Experimental Device)

As a Y-maze, a maze, in which three tracks having a length of one arm of 40 cm, a height of a wall of 13 cm, a width of a bottom of 3 cm, and a width of a top of 10 cm are each joined in the Y shape at a degree of 120, was used.

(Test Method)

A test drug (0.1, 0.3, 1, 3 and 10 mg/kg, suspended in 0.5% methyl cellulose) was orally administered once to a 5- to 6-week old ddY male mice (n=8, Japan SLC, Inc.) at 0.5 or one hour before the Y maze test started, and further, MK-801 (Sigma), which is an NMDA receptor antagonist causing cognitive impairment, was intraperitoneally administered at a dose of 0.15 mg/kg at 20 minutes before the Y-maze test started.

Further, for the mice in a control group, a vehicle (0.5% methyl cellulose) was used instead of a test drug, and physiological saline, not MK-801, was used.

For the mice in the MK-801 control group, a vehicle (0.5% methyl cellulose) was used instead of the test drug.

The above-described mice were allowed to explore freely for 8 minutes after being placed at an end of one track in the Y-maze. The number of times the mice entered the track was counted, and taken as a total entry number. The number of times the mice successively entered different three tracks (for example, when taking three arms as a, b, and c, respectively, a case where the order of the track that entered was "abccbacab" was counted as 4) was considered as a spontaneous alternation behavior number. The spontaneous alternation behavior rate was calculated by the following calculation and used as an index for a spontaneous alternation behavior:

Spontaneous alternation behavior rate=[spontaneous alternation behavior number/(total number of entries−2)]×100

A higher index value indicates the maintenance of short-term memory.

(Data Analysis)

A test for significant difference between the control group and the MK-801 control group was carried out by a Student's t-test. Further, a test for significant difference between the test drug-administered group and the MK-801 control group was carried out by a Dunnett's type multiple comparison test, and an improving effect of the test drug on learning disorder was determined. With P<0.05 in each test, it was determined that there is a significant difference.

The results that representative Example compounds of the present invention significantly improved the spontaneous alternation behavior are shown in Table below. In the Table, No. represents a Compound No., Ex represents an Example Compound No., and Dat.2 represents an effective dose.

TABLE 3

| No.   | Dat. 2            |
|-------|-------------------|
| Ex 18 | 1, 3, 10 mg/kg    |
| Ex 37 | 0.3, 1, 3, 10 mg/kg |
| Ex 76 | 1, 3, 10 mg/kg    |

As a result of the tests above, a PAM activity on an α7 nACh receptor was confirmed in the representative compounds of the formula (I). Further, as a result of the tests above, it was confirmed that the representative compounds of the formula (I) are effective in a Y-maze test. Therefore, it can be expected that the compound of the formula (I) can be used for preventing or treating dementia, cognitive impairment, schizophrenia, Alzheimer's disease, CIAS, negative symptoms of schizophrenia, inflammatory diseases, or pain.

A pharmaceutical composition containing one or two or more kinds of a compound of the formula (I) or a salt thereof as an active ingredient can be prepared using excipients that are commonly used in the art, that is, pharmaceutical excipients, pharmaceutical carriers, and the like according to a conventionally used method.

Administration can be accomplished either by oral administration via tablets, pills, capsules, granules, powders, solutions, and the like, or parenteral administration injections, such as intraarticular, intravenous or intramuscular injections, suppositories, transdermal liquid preparations, ointments, transdermal patches, transmucosal liquid preparations, transmucosal patches, inhalers, and the like.

As the solid composition for oral administration, tablets, powders, granules, or the like may be used. In such a solid composition, one or two or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains commonly used inert diluents, for example, purified water or EtOH. In addition to the inert diluent, the liquid composition may also contain auxiliary agents, such as a solubilization assisting agent, a moistening agent, and a suspending agent, sweeteners, flavors, aromatics, and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include alcohols such as EtOH. Such a composition may further contain a tonicity agent, an antiseptic, a moistening agent, an emulsifying agent, a dispersing agent, a stabilizing agent, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to use.

Examples of the agent for external use includes ointments, plasters, creams, jellies, patches, sprays, lotions, eye drops, eye ointments, and the like. The agents contain generally used ointment bases, lotion bases, aqueous or non-aqueous liquid preparations, suspensions, emulsions, or the like.

As the transmucosal agents such as an inhaler and a transnasal agent, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For the administration, an appropriate device for inhalation or insufflation can be used. For example, a compound may be administered alone or as a powder of formulated mixture, or as a solution or suspension in combination with a pharmaceutically acceptable carrier, using a known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like, or other forms.

In general oral administration, the daily dose is suitably about 0.001 to 100 mg/kg, preferably 0.003 to 30 mg/kg, and more preferably 0.01 to 10 mg/kg, per body weight, administered in one portion or in 2 to 4 divided portions. In the case of intravenous administration, the daily dose is suitably about 0.001 to 10 mg/kg per body weight, once a day or two or more times a day. In addition, a transmucosal agent is administered at a dose of about 0.001 to 10 mg/kg per body weight, once a day or two or more times a day. The dose is appropriately determined in response to the individual case by taking the symptoms, the age, and the gender, and the like into consideration.

Although varying depending on administration routes, dosage forms, administration sites, or the types of excipients and additives, the pharmaceutical composition of the present invention contains 0.01% to 100% by weight, and in one embodiment, 0.01% to 50% by weight of one or more kinds of the compound of the formula (I) or a salt thereof, which is an active ingredient.

The compound of the formula (I) can be used in combination with various agents for treating or preventing the diseases for which the compound of the formula (I) is considered to be effective. The combined preparation may be administered simultaneously, or separately and continuously, or at a desired time interval. The preparations to be co-administered may be a blend, or may be formulated individually.

EXAMPLES

Hereinbelow, the preparation methods for the compound of the formula (I) will be described in more detail with reference to Examples. Further, the present invention is not limited to the compounds described in the following Examples. Furthermore, the preparation methods for the starting compounds will be described in Preparation Examples.

Furthermore, the following abbreviations may be used in some cases in the present specification, for example, Tables below.

No.: Compound No., No./Inf: Compound No./(salt and optical activity information of the compound), Pr: Preparation Example No., Ex: Example No., Ref: preparation process (indicating that the compound was prepared by the process which is similar to the compound of Example No. or Preparation Example No. described in the column), Str: Chemical structural formula, Dat: Physicochemical data, ESI+: m/z value ([M+H]$^+$, unless otherwise specified) in ESI-MS+, APCI/ESI+: m/z value ([M+H]$^+$, unless otherwise specified) in the simultaneous measurement of APCI-MS+ and ESI-MS+, and NMR1: δ (ppm) measured by $^1$H-NMR at 400 MHz in DMSO-d$_6$ solvent. NMR signals show a representative signal.

FM: fumaric acid, TS: p-toluene sulfonic acid (tosic acid), BS: benzene sulfonic acid (besylic acid), and PA: phosphoric acid.

In No./Inf, for example, "Ex1/FM, CHR" indicates that the compound Ex1 is fumarate, optically active.

In Ref, for example, the "Ex1" in the Ex2 column indicates that Example compound Ex2 was prepared in the same manner as in the method described in Ex1.

Preparation Example 1

EtOH (150 mL) was added to KOtBu (27 g) at room temperature, and stirred until dissolved. Diethyl oxalate (35 g) was added to the reaction mixture, and oxepan-4-one (23.99 g) was added thereto. The reaction mixture was stirred for 10 minutes at room temperature and stirred for 45 minutes at 70° C. 2-cyanoacetamide (20 g) was added to the reaction mixture at 70° C., followed by cooling to room temperature and stirring at room temperature for 1 day. 1M hydrochloric acid (240 mL) was added to the reaction mixture which was then extracted with AcOEt. The organic layer was washed with brine, dried over Na$_2$SO$_4$, and then concentrated under reduced pressure to give a mixture (26.9 g) of ethyl 3-cyano-2-oxo-1,2,5,7,8,9-hexahydrooxepino[4,3-b]pyridine-4-carboxylate and ethyl 3-cyano-2-oxo-1,2,5,6,8,9-hexahydrooxepino[4,5-b]pyridine-4-carboxylate.

Preparation Example 2

Concentrated hydrochloric acid (200 mL) was added to a mixture (26.9 g) of ethyl 3-cyano-2-oxo-1,2,5,7,8,9-hexahydrooxepino[4,3-b]pyridine-4-carboxylate and ethyl 3-cyano-2-oxo-1,2,5,6,8,9-hexahydrooxepino[4,5-b]pyridine-4-carboxylate which was then stirred 120° C. for 1 day. The reaction mixture was concentrated under reduced pressure. EtOH (500 mL) was added to the residue which was then concentrated under reduced pressure to give a mixture (21.5 g) of 2-oxo-1,2,5,6,8,9-hexahydrooxepino[4,5-b]pyridine-4-carboxylic acid and 2-oxo-1,2,5,7,8,9-hexahydrooxepino[4,3-b]pyridine-4-carboxylic acid.

Preparation Example 3

A mixture of the mixture (19 g) of 2-oxo-1,2,5,6,8,9-hexahydrooxepino[4,5-b]pyridine-4-carboxylic acid and 2-oxo-1,2,5,7,8,9-hexahydrooxepino[4,3-b]pyridine-4-carboxylic acid, EtOH (200 mL), and concentrated sulfuric acid (18 g) was stirred at 90° C. for 8 hours. The reaction mixture was concentrated under reduced pressure, and H$_2$O was added thereto, followed by extraction with AcOEt. The organic layer was dried over MgSO$_4$, and concentrated under reduced pressure. The residue was purified by silica gel CC (CHCl$_3$/MeOH) to give ethyl 2-oxo-1,2,5,6,8,9-hexahydrooxepino[4,5-b]pyridine-4-carboxylate (2.36 g).

Preparation Example 4

Pyridine (270 μL) and Tf$_2$O (550 μL) were added to a mixture of ethyl 2-oxo-1,2,5,6,8,9-hexahydrooxepino[4,5-b]pyridine-4-carboxylate (700 mg) and CH$_2$Cl$_2$ (10 mL) under ice-cooling, followed by stirring under ice-cooling for 3 hours. The reaction mixture was diluted with CHCl$_3$, and H$_2$O was added to carry out liquid separation. The organic layer was washed with brine, dried over MgSO$_4$, and then concentrated under reduced pressure. The residue was purified using silica gel CC (hexane/AcOEt) to give ethyl 2-{[(trifluoromethyl)sulfonyl]oxy}-5,6,8,9-tetrahydrooxepino[4,5-b]pyridine-4-carboxylate (1.04 g).

Preparation Example 5

3-(trifluoromethyl)piperidine (750 mg) was added to a mixture of ethyl 2-{[(trifluoromethyl)sulfonyl]oxy}-5,6,8,9-tetrahydrooxepino[4,5-b]pyridine-4-carboxylate (600 mg) and DMSO (5 mL) which was then stirred at room temperature for 3 days. 3-(trifluoromethyl)piperidine (200 μL) was further added to reaction mixture which was then stirred overnight at 40° C. H$_2$O was added to the reaction mixture, followed by extraction with AcOEt. The organic layer was washed with H$_2$O-brine (1:1), dried over MgSO$_4$, and then concentrated under reduced pressure. The residue was purified by silica gel CC (hexane/AcOEt) to give ethyl 2-[3-(trifluoromethyl)piperidin-1-yl]-5,6,8,9-tetrahydrooxepino[4,5-b]pyridine-4-carboxylate (174 mg).

Preparation Example 6

Pyridine (0.788 g) was added to a mixture of ethyl 2-oxo-1,2,5,6,8,9-hexahydrooxepino[4,5-b]pyridine-4-carboxylate (2 g) and CH$_2$Cl$_2$ (10 mL), and Tf$_2$O (2.8 g) was then added thereto under ice-cooling. The reaction mixture was stirred under ice-cooling for 2 hours. The reaction mixture was diluted with CHCl$_3$, and H$_2$O was added thereto, followed by extraction with CHCl$_3$. The organic layer was washed with brine, dried over MgSO$_4$, and then concentrated under reduced pressure. The resulting residue was dissolved in DMSO (10 mL), and (2R,6S)-2,6-dimethylmorpholine (7 mL) was added thereto. The reaction mixture was stirred overnight at 40° C. The reaction mixture was diluted with AcOEt, and H$_2$O was added thereto, followed by extraction with AcOEt. The organic layer was washed successively with H$_2$O and brine, dried over MgSO$_4$, and concentrated under reduced pressure. The residue was purified by silica gel CC (hexane/AcOEt) to give ethyl 2-[(2R,6S)-2,6-dimethylmorpholin-4-yl]-5,6,8,9-tetrahydrooxepino[4,5-b]pyridine-4-carboxylate (0.562 g).

Preparation Example 7

A mixture of ethyl 2-{[(trifluoromethyl)sulfonyl]oxy}-5,6,8,9-tetrahydrooxepino[4,5-b]pyridine-4-carboxylate (850 mg), 1,4-dioxane (17 mL), 2,2,6,6-tetramethylmorpholine (660 mg), (1E,4E)-1,5-diphenylpenta-1,4-dien-3-one-palladium (3:2) (210 mg), (9,9-dimethyl-9H-xanthene-4,5-diyl)bis(diphenylphosphine) (2.66 g), and Cs$_2$CO$_3$ (1.5 g) was stirred at 140° C. for 1 hour using a microwave reactor. After the reaction mixture was diluted with AcOEt and H$_2$O, the insoluble material was removed by filtration and then the filtrate was separated. The organic layer was washed with brine, dried over MgSO$_4$, and then concentrated under reduced pressure. The residue was purified by silica gel CC (hexane/AcOEt) to give ethyl 2-(2,2,6,6-tetramethylmorpholin-4-yl)-5,6,8,9-tetrahydrooxepino[4,5-b]pyridine-4-carboxylate (495 mg).

Preparation Example 8

A 1M NaOH aqueous solution (2 mL) was added to an EtOH (30 mL) solution of ethyl 2-[(2R,6S)-2,6-dimethylmorpholin-4-yl]-5,6,8,9-tetrahydrooxepino[4,5-b]pyridine-4-carboxylate (300 mg), followed by stirring at 60° C. for 1 hour. The reaction mixture was cooled to room temperature, and 1M hydrochloric acid (2 mL) was added thereto. The reaction mixture was concentrated under reduced pressure, and H$_2$O was added thereto, followed by stirring at room temperature for 10 minutes. The solid was collected by filtration, washed with H$_2$O, and then dried under reduced pressure to give 2-[(2R,6S)-2,6-dimethylmorpholin-4-yl]-5,6,8,9-tetrahydrooxepino[4,5-b]pyridine-4-carboxylic acid (200 mg).

Preparation Example 9

A mixture of methyl 2-chloro-6-[(2R,6S)-2,6-dimethylmorpholin-4-yl]isonicotinate (4.54 g), potassium trifluoro(vinyl)borate (3.2 g), a [1,1'-bis(diphenylphosphino)ferrocene]palladium(II) dichloride dichloromethane adduct (900 mg), Et$_3$N (4.5 mL), and isopropanol (90 mL) was stirred under a nitrogen atmosphere at 80° C. for 18 hours. AcOEt and H$_2$O were added to the reaction mixture which was then extracted with AcOEt. The organic layer was dried over MgSO$_4$, and then concentrated under reduced pressure. The residue was purified by silica gel CC (hexane/AcOEt) to give methyl 2-[(2R,6S)-2,6-dimethylmorpholin-4-yl]-6-vinylisonicotinate (4.19 g).

Preparation Example 10

OsO$_4$ (2.5% tBuOH solution, 10.3 mL) was added to a mixture of methyl 2-[(2R,6S)-2,6-dimethylmorpholin-4-yl]-6-vinylisonicotinate (3.03 g), THF (90 mL) and H$_2$O (30 mL) which was then stirred at room temperature for 10 minutes. NaIO$_4$ (6.99 g) was added to the reaction mixture which was then stirred at room temperature for 3 hours. AcOEt and H$_2$O were added to the reaction mixture which was then extracted with AcOEt. The organic layer was sequentially washed with a 20% Na$_2$S$_2$O$_3$ aqueous solution and brine, dried over MgSO$_4$, and then concentrated under reduced pressure. The residue was purified by silica gel CC (hexane/AcOEt) to give methyl 2-[(2R,6S)-2,6-dimethylmorpholin-4-yl]-6-formylisonicotinate (2.67 g).

Preparation Example 11

NaBH$_4$ (400 mg) was added under a nitrogen atmosphere and under ice-cooling to a mixture of methyl 2-[(2R,6S)-2,6-dimethylmorpholin-4-yl]-6-formylisonicotinate (2.67 g) and THF (80 mL) which was then stirred at room temperature from 0° C. for 3.5 hours. AcOEt and a saturated NH$_4$Cl aqueous solution were added to the reaction mixture which was then extracted with AcOEt. The organic layer was dried over MgSO$_4$, and then concentrated under reduced pressure to give methyl 2-[(2R,6S)-2,6-dimethylmorpholin-4-yl]-6-(hydroxymethyl)isonicotinate (2.70 g).

Preparation Example 12

NBS (1.83 g) was added to a mixture of methyl 2-[(2R,6S)-2,6-dimethylmorpholin-4-yl]-6-(hydroxymethyl)isonicotinate (2.69 g) and MeCN (80 mL) which was then stirred at room temperature for 14 hours. AcOEt and H$_2$O were added to the reaction mixture which was then extracted with AcOEt. The organic layer was dried over MgSO$_4$, and then concentrated under reduced pressure. The residue was purified by silica gel CC (hexane/AcOEt) to give methyl 3-bromo-6-[(2R,6S)-2,6-dimethylmorpholin-4-yl]-2-(hydroxymethyl)isonicotinate (2.33 g).

Preparation Example 13

A mixture of methyl 3-bromo-6-[(2R,6S)-2,6-dimethylmorpholin-4-yl]-2-(hydroxymethyl)isonicotinate (800 mg), potassium trifluoro(vinyl)borate (600 mg), a [1,1'-bis(diphenylphosphino)ferrocene]palladium(II) dichloride dichloromethane adduct (330 mg), Et$_3$N (850 μL) and butan-1-ol (16 mL) was stirred under a nitrogen atmosphere at 100° C. for 5.5 hours. CHCl$_3$ and H$_2$O were added to the reaction mixture which was then extracted with CHCl$_3$. The organic layer was dried over MgSO$_4$, and then concentrated under reduced pressure. The residue was purified by silica gel CC (hexane/AcOEt) to give methyl 6-[(2R,6S)-2,6-dimethylmorpholin-4-yl]-2-(hydroxymethyl)-3-vinylisonicotinate (634 mg).

Preparation Example 14

Sodium hydride (55% mineral oil dispersion, 225 mg) was added under a nitrogen atmosphere and under ice-cooling to a mixture of methyl 6-[(2R,6S)-2,6-dimethylmorpholin-4-yl]-2-(hydroxymethyl)-3-vinylisonicotinate (630 mg) and DMF (19 mL) which was then stirred at room temperature for 20 minutes. 3-bromoprop-1-ene (440 μL) was added under ice-cooling to the reaction mixture which was then stirred at room temperature from 0° C. for 21 hours. A saturated NH$_4$Cl solution and CHCl$_3$ were added to the reaction mixture which was then extracted with CHCl$_3$. The organic layer was dried over MgSO$_4$, and then concentrated under reduced pressure. A 1M NaOH aqueous solution (5.2 mL) and THF (10 mL) were added to the residue which was then stirred at 80° C. for 2 hours. 1M hydrochloric acid (5.2 mL) was added to the reaction mixture which was then stirred at room temperature for 5 minutes. H$_2$O and CHCl$_3$ were added to the reaction mixture which was then extracted with CHCl$_3$. The organic layer was dried over MgSO$_4$, and then concentrated under reduced pressure. The residue was purified by silica gel CC (CHCl$_3$/MeOH) to give 2-[(allyloxy)methyl]-6-[(2R,6S)-2,6-dimethylmorpholin-4-yl]-3-vinylisonicotinic acid (579 mg).

Preparation Example 15

A Grubbs catalyst (75 mg) was added under a nitrogen atmosphere to a mixture of 2-[(allyloxy)methyl]-6-[(2R,6S)-2,6-dimethylmorpholin-4-yl]-3-vinylisonicotinic acid (577 mg) and CH$_2$Cl$_2$ (170 mL) which was then stirred for 4 hours under heating to reflux. The reaction mixture was concentrated under reduced pressure. The residue was purified by silica gel CC (CHCl$_3$/MeOH). EtOH (15 mL) and Pd/C with 10% water content (180 mg) were added to the residue which was then stirred under a hydrogen atmosphere at room temperature for 12 hours. The reaction mixture was diluted with MeOH, filtered through Celite, and concentrated under reduced pressure to give 2-[(2R,6S)-2,6-dimethylmorpholin-4-yl]-5,6,7,9-tetrahydrooxepino[3,4-b]pyridine-4-carboxylic acid (477 mg).

Preparation Example 16

DIPEA (6.5 mL) and (2R,6S)-2,6-dimethylmorpholine (3.5 mL) were added to a 1,4-dioxane (78 mL) solution of methyl 2,6-dichloroisonicotinate (4.0 g) which was then stirred at 100° C. for 12 hours. $H_2O$ and AcOEt were added to the reaction mixture which was then extracted with AcOEt. The organic layer was dried over $MgSO_4$, and then concentrated under reduced pressure. The residue was purified by CC (hexane/AcOEt) to give methyl 2-chloro-6-[(2R,6S)-2,6-dimethylmorpholin-4-yl]isonicotinate (4.54 g).

Preparation Example 17

A mixture of 2,2,6,6-tetramethylpiperidine (0.624 g) and THF (5 mL) was cooled in a dry ice-acetone bath, and nBuLi (2.6M hexane solution, 1.65 mL) was added thereto, followed by warming to −20° C. and stirring for 10 minutes. The reaction mixture was cooled in a dry ice-acetone bath to which a THF (5 mL) solution of methyl 2-chloro-6-[(2R,6S)-2,6-dimethylmorpholin-4-yl]isonicotinate (1.0 g) was added dropwise, followed by stirring at the same temperature for 1 hour. A THF (5 mL) solution of 4-{[tert-butyl(dimethyl)silyl]oxy}butanal (1.0 g) was added to the reaction mixture at the same temperature, followed by gradual warming to room temperature and stirring for 4 hours. $H_2O$ and brine were added to the reaction mixture which was then extracted with AcOEt and concentrated under reduced pressure. THF (6 mL) and TBAF (1M THF solution, 6 mL) were added to the residue which was then stirred at room temperature for 5 hours. $H_2O$ and brine were added to the reaction mixture which was then extracted with AcOEt. The organic layer was dried over $MgSO_4$, and then concentrated under reduced pressure. The residue was purified by silica gel CC (hexane/AcOEt) to give 4-chloro-6-[(2R,6S)-2,6-dimethylmorpholin-4-yl]-3-(3-hydroxypropyl)furo[3,4-c]pyridin-1(3H)-one (0.277 g).

Preparation Example 18

A mixture of 4-chloro-6-[(2R,6S)-2,6-dimethylmorpholin-4-yl]-3-(3-hydroxypropyl)furo[3,4-c]pyridin-1 (3H)-one (0.30 g), toluene (3 mL), $Cs_2CO_3$ (0.45 g), Pd $(OAc)_2$(20 mg), and 1,1'-binaphthalen-2-yl(di-tert-butyl)phosphine (40 mg) was stirred in a microwave reactor under an argon atmosphere at 120° C. for 4 hours. The reaction mixture was allowed to cool to room temperature and then purified by silica gel CC (hexane/AcOEt) to give 4-[(2R,6S)-2,6-dimethylmorpholin-4-yl]-7,8,9,9a-tetrahydro-2H-1,6-dioxa-5-azabenzo[cd]azulen-2-one (120 mg).

Preparation Example 19

A mixture of 4-[(2R,6S)-2,6-dimethylmorpholin-4-yl]-7,8,9,9a-tetrahydro-2H-1,6-dioxa-5-azabenzo[cd]azulen-2-one (75 mg), MeOH (10 mL), and 10% Pd/C (0.1 g) was stirred under a hydrogen atmosphere of 3.4 atmospheric pressure at room temperature for 5 hours. The reaction mixture was filtered through Celite, and then concentrated under reduced pressure. MeOH (20 mL) and 10% Pd/C (0.35 g) were added to residue which was then stirred under a hydrogen atmosphere of 3.6 atmospheric pressure at room temperature for 18 hours. The reaction mixture was filtered through Celite, concentrated under reduced pressure, and dried to give 8-[(2R,6S)-2,6-dimethylmorpholin-4-yl]-2,3,4,5-tetrahydrooxepino[2,3-b]pyridine-6-carboxylic acid (58 mg).

Preparation Example 20

1-(4-methoxyphenyl)methaneamine (91.1 g) and AcOH (16 g) were added to a mixture of ethyl 5-oxooxepane-4-carboxylate (103 g) and EtOH (500 mL) which was then stirred at 50° C. for 5 hours. The reaction mixture was concentrated under reduced pressure. AcOEt and $H_2O$ were added to the residue which was then extracted with AcOEt. The organic layer was sequentially washed with saturated a $NaHCO_3$ aqueous solution and brine, dried over $MgSO_4$, concentrated under reduced pressure, and then dried to give ethyl 5-[(4-methoxybenzyl)amino]-2,3,6,7-tetrahydrooxepine-4-carboxylate (169 g).

Preparation Example 21

NaH (60% mineral oil dispersion, 13.2 g) was added under ice-cooling to a mixture of ethyl 5-[(4-methoxybenzyl)amino]-2,3,6,7-tetrahydrooxepine-4-carboxylate (77.6 g) and THF (620 mL) which was then stirred at the same temperature for 10 minutes, and AcCl (27 mL) was added thereto, followed by stirring at 0° C. to room temperature for 6.3 hours. Under ice-cooling, the reaction mixture was added to a mixture of 1M hydrochloric acid (153 mL), brine (153 mL) and ice (150 g). AcOEt was added to the reaction mixture. The organic layer was collected, and the aqueous layer was extracted with AcOEt. The combined organic layer was washed with brine, dried over $MgSO_4$, and concentrated under reduced pressure to give ethyl 5-[acetyl(4-methoxybenzyl)amino]-2,3,6,7-tetrahydrooxepine-4-carboxylate (85.1 g).

Preparation Example 22

LHMDS (1.1M THF solution, 240 mL) was added to a mixture of ethyl 5-[acetyl(4-methoxybenzyl)amino]-2,3,6,7-tetrahydrooxepine-4-carboxylate (91.9 g) and THF (200 mL) at −65° C., followed by stirring for 1 hour, and LHMDS (1.1M THF solution, 260 mL) was added thereto, followed by further stirring at −65° C. for 1 hour. $H_2O$ and hexane were added to the reaction mixture, followed by stirring at room temperature, and the aqueous layer was collected. Concentrated hydrochloric acid (46 mL) was added to the aqueous layer which was then stirred. The precipitated solid was collected by filtration, and then dried under reduced pressure to give 4-hydroxy-1-(4-methoxybenzyl)-5,6,8,9-tetrahydrooxepino[4,5-b]pyridin-2(1H)-one (30 g).

Preparation Example 23

2-aminoethyl hydrogen sulfate (40 g) was added under ice-cooling to a mixture of KOH (17 g) and $H_2O$ (12 mL) which was then stirred at room temperature for 30 minutes, and a MeOH solution (2 mL) of (2R)-2-ethyloxirane (2 g) was added dropwise thereto. After stirring at room temperature for 2 hours, an aqueous solution (12 mL) of KOH (31 g) was added under ice-cooling, followed by stirring at 50° C. for 12 hours. The reaction solution was filtered through Celite. Di-tert-butyl dicarbonate (6 g) was added to the filtrate which was then stirred at room temperature for 2 hours. The reaction mixture was extracted with AcOEt, and the organic layer was dried over $Na_2SO_4$, and then concentrated under reduced pressure. The residue was purified by silica gel CC (hexane/AcOEt) to give tert-butyl (2R)-2-ethylmorpholine-4-carboxylate (1.0 g).

Preparation Example 24

1,1,1-trifluoro-N-phenyl-N-[(trifluoromethyl)sulfonyl]methanesulfonamide (37.11 g) was added to a mixture of 4-hydroxy-1-(4-methoxybenzyl)-5,6,8,9-tetrahydrooxepino[4,5-b]pyridin-2(1H)-one (32.95 g) and DMF (165 mL) which was then stirred at room temperature. Et$_3$N (16 mL) was added to the reaction mixture which was then stirred at room temperature for 1 hour. H$_2$O was added under ice-cooling to the reaction mixture which was then stirred and collected by filtration to give 1-(4-methoxybenzyl)-2-oxo-1,2,5,6,8,9-hexahydrooxepino[4,5-b]pyridin-4-yl trifluoromethanesulfonate (43.4 g).

Preparation Example 25

Under an argon atmosphere at 90° C., Pd$_2$ (dba)$_3$ (291 mg), dppf (422 mg), 1-(4-methoxybenzyl)-2-oxo-1,2,5,6,8,9-hexahydrooxepino[4,5-b]pyridin-4-yl trifluoromethanesulfonate (27.5 g), Zn (CN)$_2$ (4.47 g), and H$_2$O (1.4 mL) were added to DMF (140 mL) which was then stirred at 110° C. for 3 hours. NH$_4$Cl (25% aqueous solution)-28% aqueous NH$_3$—H$_2$O (4:1:4, 80 mL) was added under ice-cooling to the reaction mixture which was then stirred. The precipitated solid was collected by filtration, washed with water, and then dried under reduced pressure to give 1-(4-methoxybenzyl)-2-oxo-1,2,5,6,8,9-hexahydrooxepino[4,5-b]pyridine-4-carbonitrile (13.2 g).

Preparation Example 26

A mixture of 1-(4-methoxybenzyl)-2-oxo-1,2,5,6,8,9-hexahydrooxepino[4,5-b]pyridine-4-carbonitrile (17 g), EtOH (12 mL), and a 3M NaOH aqueous solution (45 mL) was stirred at 85° C. for 15 hours. The reaction mixture was filtered through Celite. Toluene was added to the filtrate which was then stirred and separated. Activated carbon (purified Shirasagi (registered trademark), 3.7 g) was added to the aqueous layer which was then stirred and filtered through Celite. 3M hydrochloric acid (45 mL) was added under ice-cooling to the filtrate which was then stirred. The precipitated solid was collected by filtration, and then dried under reduced pressure to give 1-(4-methoxybenzyl)-2-oxo-1,2,5,6,8,9-hexahydrooxepino[4,5-b]pyridine-4-carboxylic acid (16.7 g).

Preparation Example 27

K$_2$CO$_3$ (14 g) and CH$_3$I (21.6 g) were added to a mixture of 1-(4-methoxybenzyl)-2-oxo-1,2,5,6,8,9-hexahydrooxepino[4,5-b]pyridine-4-carboxylic acid (16.7 g) and CH$_3$CN (167 mL) which was then stirred at 45° C. for 4.5 hours. The insoluble material of the reaction mixture was separated by filtration, and then the filtrate was concentrated under reduced pressure. H$_2$O was added to the residue which was then stirred at room temperature and stirred under ice-cooling. The precipitated solid was collected by filtration to give methyl 1-(4-methoxybenzyl)-2-oxo-1,2,5,6,8,9-hexahydrooxepino[4,5-b]pyridine-4-carboxylate (16.3 g).

Preparation Example 28

Under a nitrogen atmosphere, a mixture of CH$_2$Cl$_2$ (110 mL) and Tf$_2$O (36.7 g) was added to a mixture of methyl 1-(4-methoxybenzyl)-2-oxo-1,2,5,6,8,9-hexahydrooxepino[4,5-b]pyridine-4-carboxylate (22.3 g), CH$_2$Cl$_2$ (220 mL), and pyridine (15.4 g) which was then stirred under ice-cooling for 2 hours, and Tf$_2$O (5.5 g) was further added thereto, followed by stirring at the same temperature for 1 hour. Hexane and AcOEt were added to the reaction mixture which was then concentrated under reduced pressure, and hexane, AcOEt and H$_2$O were added thereto, followed by liquid separation. The organic layer was sequentially washed with a saturated NaHCO$_3$ aqueous solution and H$_2$O, and concentrated under reduced pressure. The residue was purified by silica gel CC (hexane/AcOEt) to give methyl 2-{[(trifluoromethyl)sulfonyl]oxy}-5,6,8,9-tetrahydrooxepino[4,5-b]pyridine-4-carboxylate (22.3 g).

Preparation Example 29

(2R,6S)-2,6-dimethylmorpholine (13.9 g) was added to a mixture of methyl 2-{[(trifluoromethyl)sulfonyl]oxy}-5,6,8,9-tetrahydrooxepino[4,5-b]pyridine-4-carboxylate (8.55 g) and DMSO (43 mL) which was then stirred at 50° C. for 17 hours. Hexane-AcOEt (1:1) was added to the reaction mixture, and H$_2$O was added thereto under ice-cooling, followed by stirring at room temperature. The organic layer was collected, and the aqueous layer was extracted with hexane-AcOEt (1:1). The combined organic layer was washed with a 1% citric acid aqueous solution and 20% physiological saline, dried over MgSO$_4$, and concentrated under reduced pressure. AcOEt (18 mL) and seed crystals of methyl 2-[(2R,6S)-2,6-dimethylmorpholin-4-yl]-5,6,8,9-tetrahydrooxepino[4,5-b]pyridine-4-carboxylate hydrochloride were added to the residue, and hydrogen chloride (4M AcOEt solution, 6.7 mL) was added thereto under ice-cooling, followed by stirring at room temperature for 20 minutes. iPr$_2$O (38 mL) was added to the reaction mixture which was then stirred at room temperature for 18 hours. The precipitate was collected by filtration, and then dried under reduced pressure to give methyl 2-[(2R,6S)-2,6-dimethylmorpholin-4-yl]-5,6,8,9-tetrahydrooxepino[4,5-b]pyridine-4-carboxylate hydrochloride (6.46 g).

Preparation Example 30

A 50% NaOH aqueous solution (6.23 mL) was added to a MeOH (170 mL) solution of methyl 2-[(2R,6S)-2,6-dimethylmorpholin-4-yl]-5,6,8,9-tetrahydrooxepino[4,5-b]pyridine-4-carboxylate hydrochloride (17.0 g) which was then stirred at 50° C. for 7 hours. MeOH (50 mL) was added to the reaction mixture, and under ice-cooling, concentrated H$_2$SO$_4$ (2.43 g) was added thereto, and then CHCl$_3$ and Na$_2$SO$_4$ were added. The reaction mixture was stirred at room temperature. The reaction mixture was filtered through Celite and washed with CHCl$_3$-MeOH (4:1). The filtrate was concentrated under reduced pressure. CHCl$_3$-MeOH (9:1) was added to the residue, and the insoluble material was separated by filtration. The filtrate was concentrated under reduced pressure. MeCN was added to the residue which was then stirred under heating to reflux. The precipitated solid was collected by filtration, and then dried under reduced pressure to give 2-[(2R,6S)-2,6-dimethylmorpholin-4-yl]-5,6,8,9-tetrahydrooxepino[4,5-b]pyridine-4-carboxylic acid (12.2 g).

Preparation Example 31

A Ghosez reagent (4.87 g) was added under ice-cooling to a mixture of 1-(4-methoxybenzyl)-2-oxo-1,2,5,6,8,9-hexahydrooxepino[4,5-b]pyridine-4-carboxylic acid (8 g) and CH$_2$Cl$_2$ (120 mL) which was then stirred at room temperature for 2 hours. Further, a mixture of 5-chloropyridine-2-amine (3.44 g), pyridine (5.76 g) and CH$_2$Cl$_2$ (40 mL) was added under ice-cooling to the reaction mixture which was then stirred at room temperature for 1 day. H$_2$O was added to the reaction mixture which was then extracted with CH$_2$Cl$_2$. The organic layer was washed with brine, dried over MgSO$_4$, and then concentrated under reduced pressure. The residue was washed with iPrOH under heating to reflux, collected by filtration, and then dried under reduced pressure to give N-(5-chloropyridin-2-yl)-1-(4-methoxybenzyl)-2-oxo-1,2,5,6,8,9-hexahydrooxepino[4,5-b]pyridine-4-carboxamide (5.30 g).

Preparation Example 32

A mixture of 1-(4-methoxybenzyl)-2-oxo-1,2,5,6,8,9-hexahydrooxepino[4,5-b]pyridine-4-carboxylic acid (3 g), WSC hydrochloride (2.1 g), pyridazine-3-amine (1.1 g), MeCN (30 mL), Et$_3$N (1.1 g), and HOBt (1.35 g) was stirred at 60° C. for 1 day. The reaction mixture was concentrated under reduced pressure. The residue was purified by silica gel CC (CHCl$_3$/MeOH) to give 1-(4-methoxybenzyl)-2-oxo-N-(pyridazin-3-yl)-1,2,5,6,8,9-hexahydrooxepino[4,5-b]pyridine-4-carboxamide (3.55 g).

Preparation Example 33

A mixture of 1-(4-methoxybenzyl)-2-oxo-1,2,5,6,8,9-hexahydrooxepino[4,5-b]pyridine-4-carboxylic acid (980 mg), pyrazine-2-amine (567 mg), WSC hydrochloride (685 mg), DMAP (730 mg) and CH$_2$Cl$_2$ (30 mL) was stirred at 50° C. for 1 day. The reaction mixture was concentrated under reduced pressure, and purified by silica gel CC (CHCl$_3$/MeOH) to give 1-(4-methoxybenzyl)-2-oxo-N-(pyrazin-2-yl)-1,2,5,6,8,9-hexahydrooxepino[4,5-b]pyridine-4-carboxamide (662 mg).

Preparation Example 34

Under an argon atmosphere, a mixture of CH$_2$Cl$_2$ (10 mL) and Tf$_2$O (4.92 g) was added under ice-cooling to a mixture of 1-(4-methoxybenzyl)-2-oxo-N-(pyridazin-3-yl)-1,2,5,6,8,9-hexahydrooxepino[4,5-b]pyridine-4-carboxamide (3.55 g), CH$_2$Cl$_2$ (50 mL) and pyridine (2.1 g), followed by stirring at the same temperature for 2 hours, and further, under ice-cooling, Tf$_2$O (740 mg) was added thereto, followed by stirring at room temperature for 1 day. The reaction mixture was concentrated under reduced pressure. The residue was purified by silica gel CC (hexane/AcOEt) to give 4-(pyridazin-3-ylcarbamoyl)-5,6,8,9-tetrahydrooxepino[4,5-b]pyridin-2-yl trifluoromethanesulfonate (1.61 g).

Preparation Example 35

Hydrogen chloride (4M AcOEt solution, 3 mL) was added to a MeOH solution (10 mL) of tert-butyl (2R)-2-ethylmorpholine-4-carboxylate (1.0 g) at room temperature, followed by stirring at the same temperature for 14 hours. The reaction solution was concentrated under reduced pressure to give (2R)-2-ethylmorpholine hydrochloride (800 mg).

Example 1

DIPEA (120 µL) was added to a mixture of 2-[(3S)-3-(trifluoromethyl)piperidin-1-yl]-5,6,8,9-tetrahydrooxepino[4,5-b]pyridine-4-carboxylic acid (120 mg), pyridazine-3-amine (70 mg), HATU (200 mg) and NMP (6 mL) which was then stirred at 60° C. for 2 days. The reaction mixture was allowed to cool to room temperature and H$_2$O was added thereto, followed by extraction with AcOEt. The organic layer was dried over MgSO$_4$, and concentrated under reduced pressure. The residue was purified by silica gel CC (CHCl$_3$/MeOH), and then purified by silica gel CC (hexane/AcOEt). The resulting compound was dissolved in a mixed solution of EtOH-Et$_2$O, and fumaric acid (33 mg) was added thereto. The precipitate was collected by filtration to give N-(pyridazin-3-yl)-2-[(3S)-3-(trifluoromethyl)piperidin-1-yl]-5,6,8,9-tetrahydrooxepino[4,5-b]pyridine-4-carboxamide fumarate (107 mg).

Example 9

A mixture of 2-(2,2,6,6-tetramethylmorpholin-4-yl)-5,6,8,9-tetrahydrooxepino[4,5-b]pyridine-4-carboxylic acid (99 mg), pyridazine-3-amine (26 mg), WSC hydrochloride (114 mg), DMAP (72 mg) and CH$_2$Cl$_2$ (3 mL) was stirred at 50° C. for 3 hours. The reaction mixture was diluted with CHCl$_3$, purified by silica gel CC (CHCl$_3$/MeOH), and then purified by silica gel CC (hexane/AcOEt). The resulting compound was dissolved in AcOEt (5 mL), and hydrogen chloride (4M AcOEt solution, 70 µL) was added thereto, followed by stirring at room temperature. The mixture was concentrated under reduced pressure to give N-(pyridazin-3-yl)-2-(2,2,6,6-tetramethylmorpholin-4-yl)-5,6,8,9-tetrahydrooxepino[4,5-b]pyridine-4-carboxamide hydrochloride (32 mg).

Example 18

A mixture of 2-[(2R,6S)-2,6-dimethylmorpholin-4-yl]-5,6,8,9-tetrahydrooxepino[4,5-b]pyridine-4-carboxylic acid (100 mg), CH$_2$Cl$_2$ (3 mL), and a Ghosez reagent (87 µL) was stirred at room temperature for 30 minutes. 5-chloropyridine-2-amine (51 mg) and pyridine (52 µL) were added to the reaction mixture which was then stirred at room temperature for 3 hours. The reaction mixture was diluted with CHCl$_3$, purified by silica gel CC (CHCl$_3$/MeOH), and then purified by silica gel CC (hexane/AcOEt). EtOH (2 mL) and hydrogen chloride (4M AcOEt solution, 1 mL) were added to the resulting compound which was then stirred at room temperature for 30 minutes. The mixture was concentrated under reduced pressure. The residue was solidified with EtOH and Et$_2$O to give N-(5-chloropyridin-2-yl)-2-[(2R,6S)-2,6-dimethylmorpholin-4-yl]-5,6,8,9-tetrahydrooxepino[4,5-b]pyridine-4-carboxamide hydrochloride (26.6 mg).

Example 32

2-butanone (5 mL) and p-toluene sulfonic acid monohydrate (43 mg) were added to N-(5-chloropyridin-2-yl)-2-[(2R,6S)-2,6-dimethylmorpholin-4-yl]-5,6,8,9-tetrahydrooxepino[4,5-b]pyridine-4-carboxamide (104 mg), followed by stirring at room temperature for 30 minutes. The mixture was concentrated under reduced pressure. 2-butanone (10 mL) was added to the residue and H$_2$O (1 mL) was added thereto at 60° C., followed by stirring. The mixture was stirred at room temperature for 1 day. Then, the precipitated solid was collected by filtration and dried under reduced pressure to give N-(5-chloropyridin-2-yl)-2-[(2R,6S)-2,6-dimethylmorpholin-4-yl]-5,6,8,9-tetrahydrooxepino[4,5-b]pyridine-4-carboxamide p-toluenesulfonate (64 mg).

Example 33

2-butanone (5.0 mL) and benzene sulfonic acid (41 mg) were added to N-(5-chloropyridin-2-yl)-2-[(2R,6S)-2,6-dimethylmorpholin-4-yl]-5,6,8,9-tetrahydrooxepino[4,5-b]pyridine-4-carboxamide (108 mg), followed by stirring at 60° C. for 30 minutes. The mixture was concentrated under reduced pressure. 2-butanone (5 mL) was added to the residue which was then stirred at 60° C., followed by stirring at room temperature for 1 day. The precipitated solid was collected by filtration and dried under reduced pressure to give N-(5-chloropyridin-2-yl)-2-[(2R,6S)-2,6-dimethylmorpholin-4-yl]-5,6,8,9-tetrahydrooxepino[4,5-b]pyridine-4-carboxamide benzenesulfonate (104 mg).

Example 69

(2S)-2-methylpiperidine (83 mg) and DIPEA (71 mg) were added to a mixture of 4-(pyridazin-3-ylcarbamoyl)-5,6,8,9-tetrahydrooxepino[4,5-b]pyridin-2-yl trifluoromethanesulfonate (70 mg) and NMP (1 mL) which was then stirred in a microwave reactor at 180° C. for 30 minutes. The reaction mixture was diluted with AcOEt, and H₂O was added thereto, followed by liquid separation. The organic layer was washed with brine, dried over MgSO₄, and then concentrated under reduced pressure. The residue was purified by silica gel CC (hexane/AcOEt). The resulting compound was suspended in EtOH (5 mL) to which hydrogen chloride (4M AcOEt solution, 1 mL) was then added, followed by stirring at room temperature for 15 minutes and concentration under reduced pressure. Et₂O was added to the residue, and the insoluble material was collected by filtration and dried under reduced pressure to give 2-[(2S)-2-methylpiperidin-1-yl]-N-(pyridazin-3-yl)-5,6,8,9-tetrahydrooxepino[4,5-b]pyridine-4-carboxamide hydrochloride (22 mg).

Compounds of Preparation Examples and Examples shown in Tables below were prepared in the same manner as in Preparation Examples or Examples described above.

TABLE 4

| No./Inf | Str |
| --- | --- |
| Pr1 | (structure: ethyl ester, CN, oxepino-pyridinone) + (structure: ethyl ester, CN, oxepino-pyridinone isomer) |
| Pr2 | (structure: carboxylic acid, oxepino-pyridinone) + |

TABLE 4-continued

| No./Inf | Str |
| --- | --- |
| | (structure: carboxylic acid OH, oxepino-pyridinone) |
| Pr3 | (structure: ethyl ester OEt, oxepino-pyridinone) |
| Pr4 | (structure: ethyl ester OEt, oxepino-pyridine-OTf) |
| Pr5 | (structure: ethyl ester OEt, oxepino-pyridine-N-piperidinyl-CF₃) |
| Pr5-1/CHR | (structure: methyl ester OMe, oxepino-pyridine-N-pyrrolidinyl-OMe) |
| Pr5-2/CHR | (structure: methyl ester OMe, oxepino-pyridine-N-morpholinyl-Et Me) |
| Pr5-3/CHR | (structure: methyl ester OMe, oxepino-pyridine-N-morpholinyl-Et Me) |

TABLE 4-continued
| No./Inf | Str |
|---|---|
| Pr5-4 | 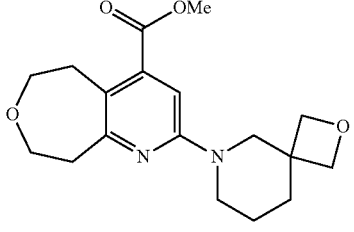 [SMILES: COC(=O)c1cc(N2CCCC3(COC3)C2)nc2c1CCOCC2] |
| Pr5-5 | 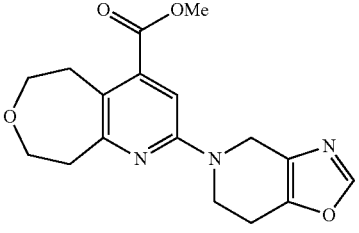 |
TABLE 5
| No./Inf | Str |
|---|---|
| Pr5-6/CHR | 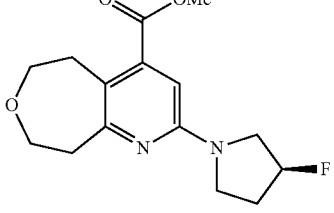 |
| Pr5-7/CHR | 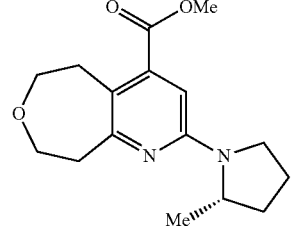 [SMILES: COC(=O)c1cc(N2CCC[C@@H]2C)nc2c1CCOCC2] |
| Pr5-8/CHR | 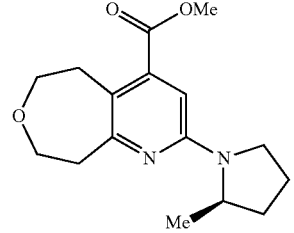 |
| Pr5-9 | 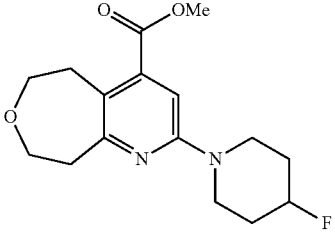 [SMILES: COC(=O)c1cc(N2CCC(F)CC2)nc2c1CCOCC2] |
TABLE 5-continued
| No./Inf | Str |
|---|---|
| Pr5-10 | 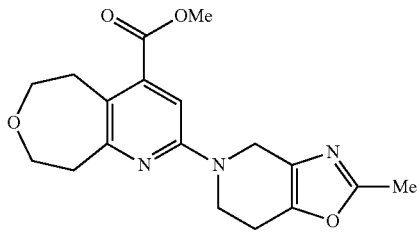 [SMILES: COC(=O)c1cc(N2CCc3oc(C)nc3C2)nc2c1CCOCC2] |
| Pr6 | 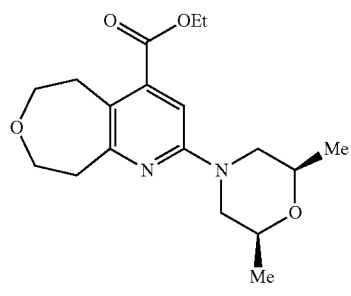 [SMILES: CCOC(=O)c1cc(N2C[C@@H](C)O[C@@H](C)C2)nc2c1CCOCC2] |
| Pr6-1/CHR | 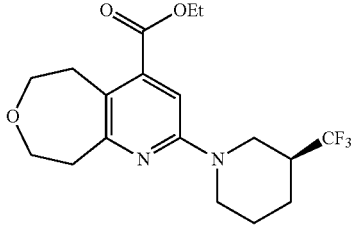 |
| Pr6-2/CHR | 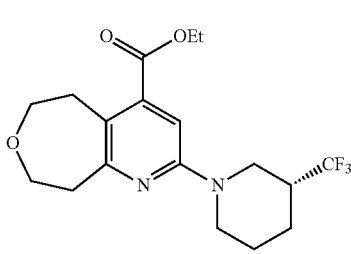 |
| Pr6-3 | 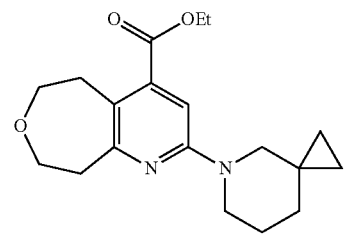 [SMILES: CCOC(=O)c1cc(N2CCCC3(CC3)C2)nc2c1CCOCC2] |
| Pr7 | 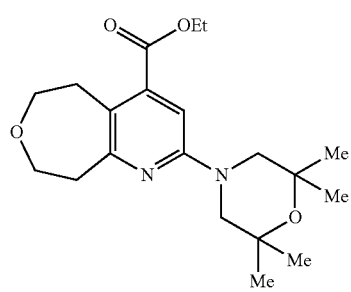 [SMILES: CCOC(=O)c1cc(N2CC(C)(C)OC(C)(C)C2)nc2c1CCOCC2] |

TABLE 6
| No./Inf | Str |
|---|---|
| Pr7-1 | 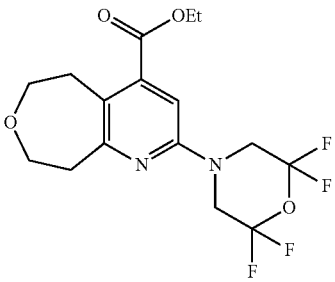 [SMILES: CCOC(=O)c1cc(N2CC(F)(F)OC(F)(F)C2)nc2c1CCOCC2] |
| Pr8 | 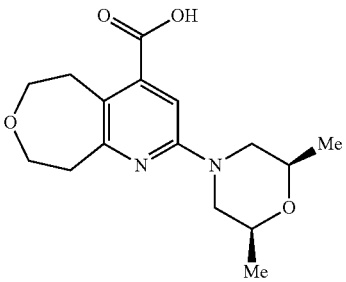 [SMILES: C[C@@H]1CN(c2cc(C(=O)O)c3c(n2)CCOCC3)C[C@H](C)O1] |
| Pr8-1/CHR | 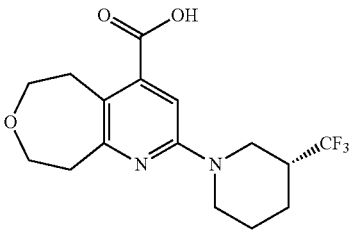 |
| Pr8-2/CHR | 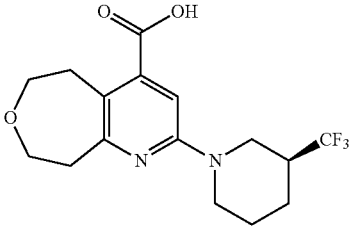 [SMILES: O=C(O)c1cc(N2CCC[C@H](C(F)(F)F)C2)nc2c1CCOCC2] |
| Pr8-3 | 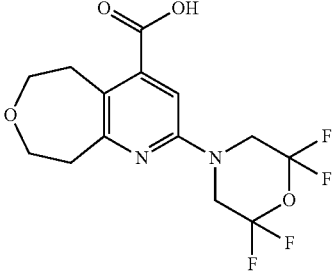 [SMILES: O=C(O)c1cc(N2CC(F)(F)OC(F)(F)C2)nc2c1CCOCC2] |
| Pr8-4 | 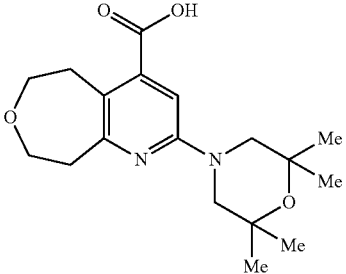 [SMILES: CC1(C)CN(c2cc(C(=O)O)c3c(n2)CCOCC3)CC(C)(C)O1] |
TABLE 6-continued
| No./Inf | Str |
|---|---|
| Pr8-5 | 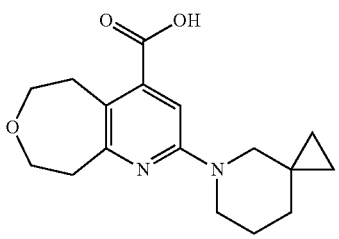 [SMILES: O=C(O)c1cc(N2CCCC3(CC3)C2)nc2c1CCOCC2] |
| Pr8-6 | 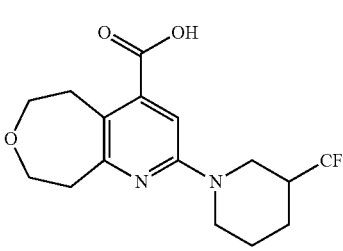 |
| Pr8-7 | 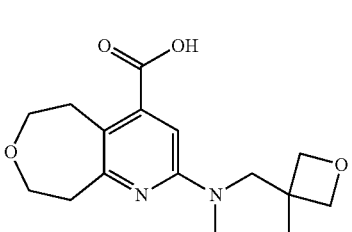 |
| Pr8-8/CHR | 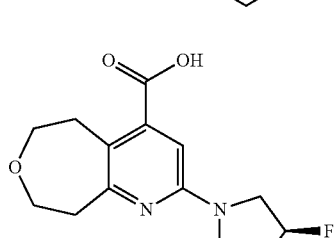 |
| Pr8-9/CHR | 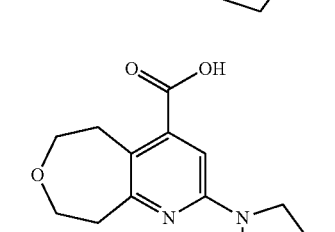 |
| Pr8-10 | 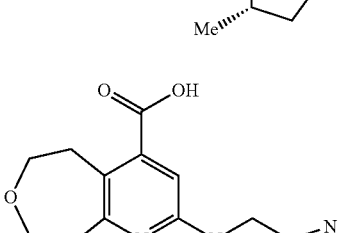 |

TABLE 7
| No./Inf | Str |
|---|---|
| Pr8-11/CHR | 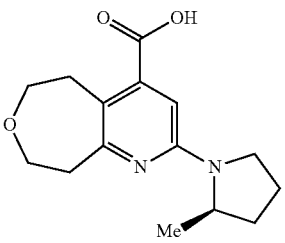 [SMILES: C[C@@H]1CCCN1c1cc(C(=O)O)c2c(n1)CCOCC2] |
| Pr8-12 | 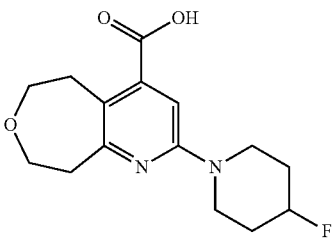 [SMILES: O=C(O)c1cc(N2CCC(F)CC2)nc2c1CCOCC2] |
| Pr8-13/CHR | 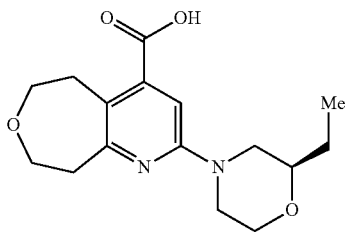 [SMILES: CC[C@@H]1CN(c2cc(C(=O)O)c3c(n2)CCOCC3)CCO1] |
| Pr8-14/CHR | 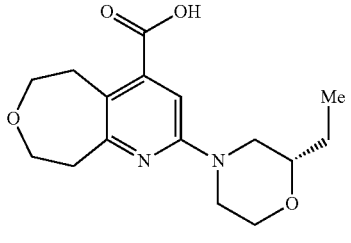 [SMILES: CC[C@H]1CN(c2cc(C(=O)O)c3c(n2)CCOCC3)CCO1] |
| Pr8-15 | 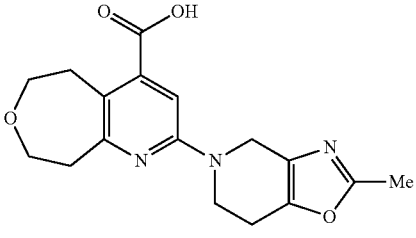 [SMILES: Cc1nc2c(o1)CCN(c1cc(C(=O)O)c3c(n1)CCOCC3)C2] |
| Pr8-16/CHR | 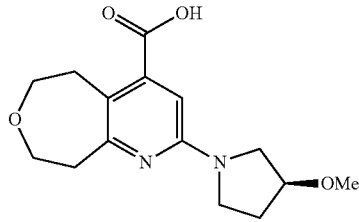 [SMILES: CO[C@H]1CCN(c2cc(C(=O)O)c3c(n2)CCOCC3)C1] |
TABLE 7-continued
| No./Inf | Str |
|---|---|
| Pr9 | 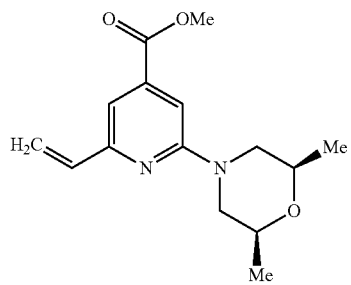 [SMILES: C=Cc1cc(C(=O)OC)cc(N2C[C@@H](C)O[C@@H](C)C2)n1] |
| Pr10 | 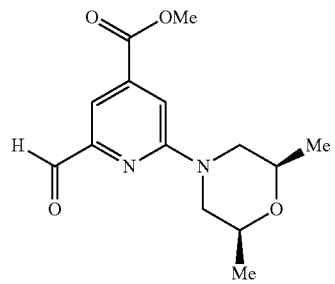 [SMILES: COC(=O)c1cc(C=O)nc(N2C[C@@H](C)O[C@@H](C)C2)c1] |
| Pr11 | 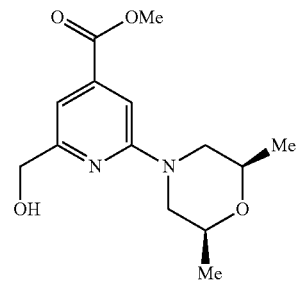 [SMILES: COC(=O)c1cc(CO)nc(N2C[C@@H](C)O[C@@H](C)C2)c1] |
| Pr12 | 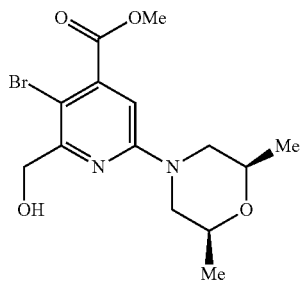 [SMILES: COC(=O)c1cc(N2C[C@@H](C)O[C@@H](C)C2)nc(CO)c1Br] |
TABLE 8
| No./Inf | Str |
|---|---|
| Pr13 | 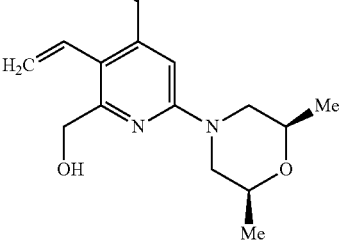 |

TABLE 8-continued

| No./Inf | Str |
|---|---|
| Pr14 | (methyl pyridine-4-carboxylate with vinyl, allyloxymethyl, and (2S,6R)-2,6-dimethylmorpholin-4-yl substituents) |
| Pr15 | (6,7,8,9-tetrahydro-5H-oxepino[3,2-b]pyridine-4-carboxylic acid with (2S,6R)-2,6-dimethylmorpholin-4-yl substituent) |
| Pr16 | (methyl 6-chloro-2-((2S,6R)-2,6-dimethylmorpholin-4-yl)pyridine-4-carboxylate) |
| Pr17 | (chloro-substituted furo-pyridinone with 3-hydroxypropyl chain and (2S,6R)-2,6-dimethylmorpholin-4-yl) |
| Pr18 | (fused tricyclic lactone-pyridine with (2S,6R)-2,6-dimethylmorpholin-4-yl) |

TABLE 8-continued

| No./Inf | Str |
|---|---|
| Pr19 | (6,7,8,9-tetrahydro-5H-oxepino[3,2-b]pyridine-4-carboxylic acid with (2S,6R)-2,6-dimethylmorpholin-4-yl) |
| Pr20 | (ethyl 5-(PMB-amino)-2,3,6,7-tetrahydrooxepine-4-carboxylate) |
| Pr21 | (ethyl 5-(N-acetyl-N-PMB-amino)-2,3,6,7-tetrahydrooxepine-4-carboxylate) |
| Pr22 | (4-hydroxy-1-PMB-oxepino[3,2-b]pyridin-2(1H)-one, partially saturated) |

TABLE 9

| No./Inf | Str |
|---|---|
| Pr23/CHR | ((R)-4-Boc-2-ethylmorpholine) |
| Pr23-1/CHR | ((S)-4-Boc-2-ethylmorpholine) |
| Pr24 | (4-OTf-1-PMB-oxepino[3,2-b]pyridin-2(1H)-one, partially saturated) |

TABLE 9-continued
| No./Inf | Str |
|---|---|
| Pr25 | 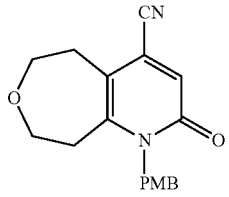 |
| Pr26 | 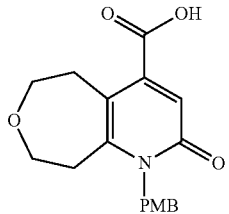 |
| Pr27 | 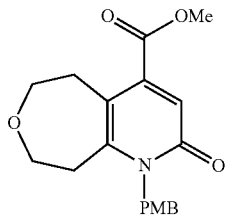 |
| Pr28 | 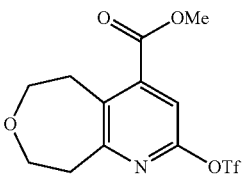 [SMILES: COC(=O)c1cc(OS(=O)(=O)C(F)(F)F)nc2c1CCOCC2] |
| Pr29/HCl | 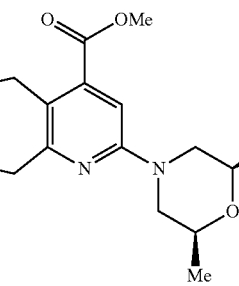 |
| Pr30 | 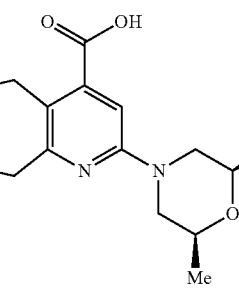 |
TABLE 9-continued
| No./Inf | Str |
|---|---|
| Pr31 | 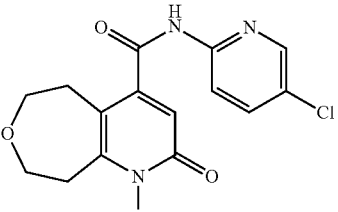 |
TABLE 10
| No./Inf | Str |
|---|---|
| Pr31-1 | 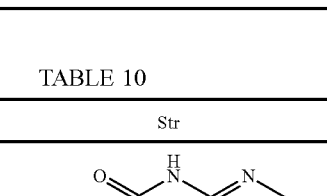 |
| Pr32 | 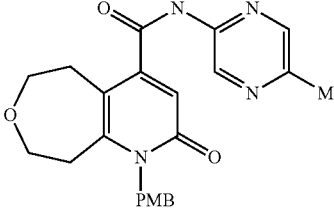 |
| Pr32-1 | 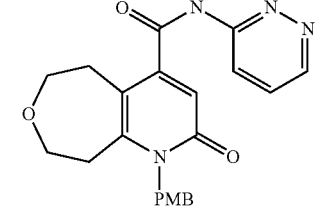 |
| Pr32-2 | 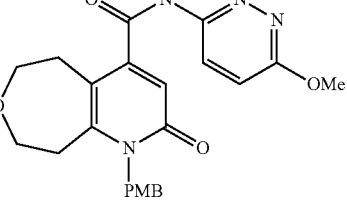 |
| Pr33 | 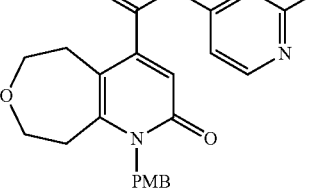 |

TABLE 10-continued
| No./Inf | Str |
|---|---|
| Pr34 | 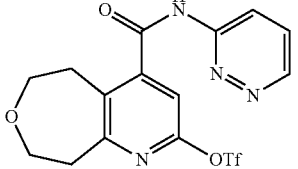 |
| Pr34-1 | 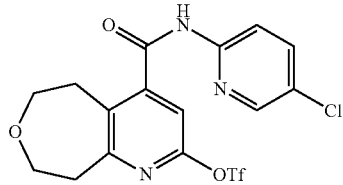 [SMILES: O=C(Nc1ccc(Cl)cn1)c1cc(OS(=O)(=O)C(F)(F)F)nc2c1CCOCC2] |
| Pr34-2 |  |
| Pr34-3 | 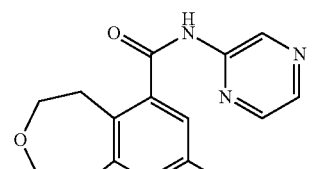 |
| Pr34-4 | 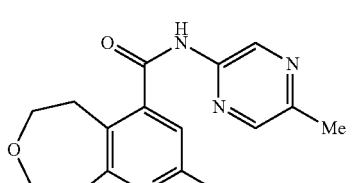 |
| Pr34-5 | 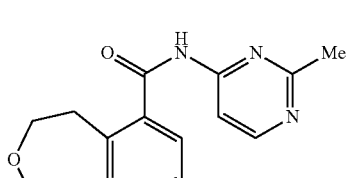 |
| Pr35/HCl CHR | 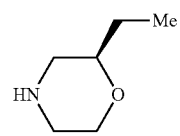 |
| Pr35-1/HCl CHR | 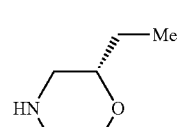 |
TABLE 11
| No./Inf | Str |
|---|---|
| Ex1/FM CHR | 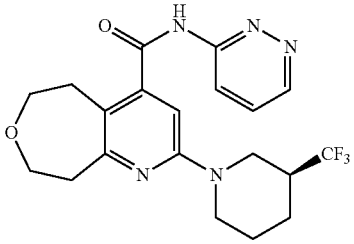 [SMILES: O=C(Nc1cccnn1)c1cc(N2CCC[C@H](C(F)(F)F)C2)nc2c1CCOCC2] |
| Ex2/HCl | 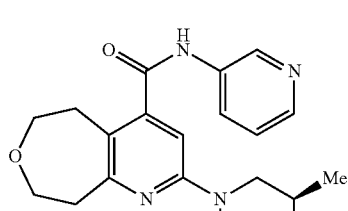 |
| Ex3/HCl | 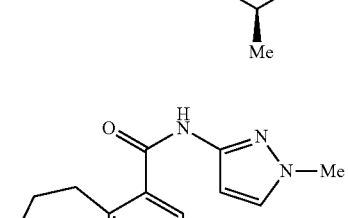 |
| Ex4 | 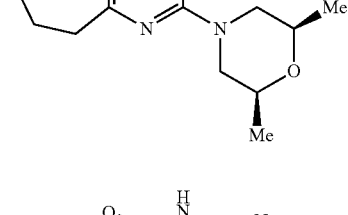 |
| Ex5 | 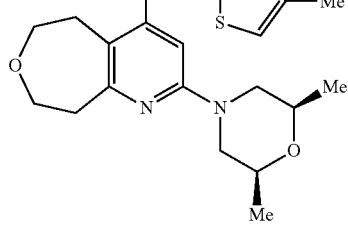 |

TABLE 11-continued

| No./Inf | Str |
|---|---|
| Ex6 | |
| Ex7/FM CHR | |
| Ex8/FM | |
| Ex9/HCl | |
| Ex10 | |

TABLE 12

| No./Inf | Str |
|---|---|
| Ex11 | |
| Ex12 | |
| Ex13 | |
| Ex14 | |
| Ex15 | |

TABLE 12-continued
| No./Inf | Str |
|---|---|
| Ex16 | 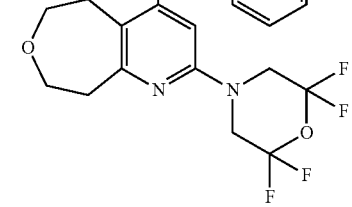 |
| Ex17/HCl | |
| Ex18/HCl | |
| Ex19/FM | |
| Ex20 | |
TABLE 13
| No./Inf | Str |
|---|---|
| Ex21 | 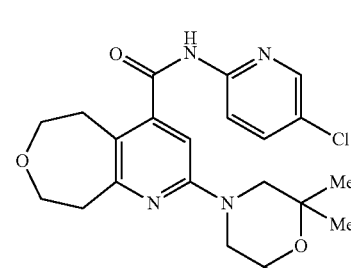 |
| Ex22 | |
| Ex23 | |
| Ex24 | |
| Ex25 | |

TABLE 13-continued
| No./Inf | Str |
|---|---|
| Ex26 | 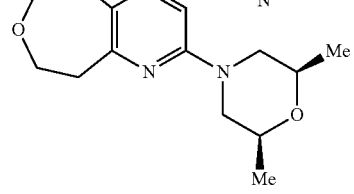 |
| Ex27 | |
| Ex28 | |
| Ex29 | |
| Ex30 | |
TABLE 14
| No./Inf | Str |
|---|---|
| Ex31/HCl | 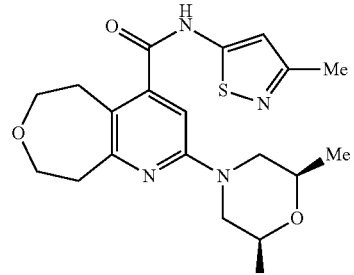 |
| Ex32/TS | |
| Ex33/BS | |
| Ex34 | |
| Ex35 | |

TABLE 14-continued

| No./Inf | Str |
|---|---|
| Ex36/CHR | (structure) |
| Ex37/PA CHR | (structure) |
| Ex38/CHR | (structure) |
| Ex39/HCl CHR | (structure) |
| Ex40/HCl CHR | (structure) |

TABLE 15

| No./Inf | Str |
|---|---|
| Ex41/CHR | (structure) |
| Ex42/CHR | (structure) |
| Ex43/HCl CHR | (structure) |
| Ex44/HCl CHR | (structure) |
| Ex45/CHR | (structure) |
| Ex46/HCl CHR | (structure) |

TABLE 15-continued

| No./Inf | Str |
|---|---|
| Ex47/HCl CHR | |
| Ex48/HCl CHR | |
| Ex49/CHR | |
| Ex50 | |

TABLE 16

| No./Inf | Str |
|---|---|
| Ex51 | |

TABLE 16-continued

| No./Inf | Str |
|---|---|
| Ex52/CHR | |
| Ex53 | |
| Ex54/HCl CHR | |
| Ex55/HCl CHR | |
| Ex56/HCl | |
| Ex57 | |

TABLE 16-continued

| No./Inf | Str |
|---|---|
| Ex58 | (structure) |
| Ex59 | (structure) |
| Ex60 | (structure) |

TABLE 17

| No./Inf | Str |
|---|---|
| Ex61/HCl | (structure) |
| Ex62/HCl | (structure) |

TABLE 17-continued

| No./Inf | Str |
|---|---|
| Ex63/CHR | (structure) |
| Ex64 | (structure) |
| Ex65/HCl | (structure) |
| Ex66/HCl CHR | (structure) |
| Ex67 | (structure) |

TABLE 17-continued

| No./Inf | Str |
|---|---|
| Ex68/HCl | |
| Ex69/HCl CHR | |
| Ex70/HCl CHR | |

TABLE 18

| No./Inf | Str |
|---|---|
| Ex71/HCl CHR | |
| Ex72/HCl CHR | |
| Ex73/HCl CHR | |
| Ex74/HCl CHR | |
| Ex75/BS CHR | |
| Ex76/BS CHR | |
| Ex77/CHR | |
| Ex78/HCl | |

TABLE 19

| No. | Ref | Dat | No. | Ref | Dat |
|---|---|---|---|---|---|
| Pr1 | Pr1 | ESI+ 263 | Pr9 | Pr9 | ESI+ 277 |
| Pr2 | Pr2 | APCI/ESI+ 210 | Pr10 | Pr10 | ESI+ 279 |
| Pr3 | Pr3 | ESI+ 238 | Pr11 | Pr11 | ESI+ 281 |
| Pr4 | Pr4 | APCI/ESI+ 370 | Pr12 | Pr12 | ESI+ 361 |
| Pr5 | Pr5 | ESI+ 373 | Pr13 | Pr13 | ESI+ 307 |
| Pr5-1 | Pr5 | ESI+ 307 | Pr14 | Pr14 | ESI+ 333 |
| Pr5-2 | Pr5 | ESI+ 321 | Pr15 | Pr15 | ESI+ 307 |
| Pr5-3 | Pr5 | ESI+ 321 | Pr16 | Pr16 | ESI+ 285, 287 |
| Pr5-4 | Pr5 | ESI+ 333 | Pr17 | Pr17 | ESI+ 341 |
| Pr5-5 | Pr5 | APCI/ESI+ 330 | Pr18 | Pr18 | ESI+ 305 |
| Pr5-6 | Pr5 | ESI+ 295 | Pr19 | Pr19 | APCI/ESI+ 307 |
| Pr5-7 | Pr5 | ESI+ 291 | Pr20 | Pr20 | ESI+ 306 |
| Pr5-8 | Pr5 | ESI+ 291 | Pr21 | Pr21 | ESI+ 348 |
| Pr5-9 | Pr5 | APCI/ESI+ 309 | Pr22 | Pr22 | APCI/ESI+ 302 |
| Pr5-10 | Pr5 | ESI+ 344 | Pr23 | Pr23 | ESI+ 238[M + Na]+ |
| Pr6 | Pr6 | ESI+ 335 | Pr23-1 | Pr23 | ESI+ 238[M + Na]+ |
| Pr6-1 | Pr6 | ESI+ 373 | Pr24 | Pr24 | APCI/ESI+ 434 |
| Pr6-2 | Pr6 | ESI+ 373 | Pr25 | Pr25 | ESI+ 311 |
| Pr6-3 | Pr6 | ESI+ 331 | Pr26 | Pr26 | ESI+ 330 |
| Pr7 | Pr7 | APCI/ESI+ 363 | Pr27 | Pr27 | ESI+ 344 |
| Pr7-1 | Pr7 | APCI/ESI+ 379 | Pr28 | Pr28 | ESI+ 356 |
| Pr8 | Pr8 | ESI+ 307 | Pr29 | Pr29 | ESI+ 321 |
| Pr8-1 | Pr8 | ESI+ 345 | Pr30 | Pr30 | ESI+ 307 |
| Pr8-2 | Pr8 | ESI+ 345 | Pr31 | Pr31 | ESI+ 440, 442 |
| Pr8-3 | Pr8 | ESI+ 351 | Pr31-1 | Pr31 | ESI+ 421 |
| Pr8-4 | Pr8 | ESI+ 335 | Pr32 | Pr32 | ESI+ 407 |
| Pr8-5 | Pr8 | ESI+ 303 | Pr32-1 | Pr32 | ESI+ 437 |
| Pr8-6 | Pr8 | ESI+ 345 | Pr32-2 | Pr32 | ESI+ 421 |
| Pr8-7 | Pr8 | ESI+ 319 | Pr33 | Pr33 | ESI+ 407 |
| Pr8-8 | Pr8 | ESI+ 281 | Pr34 | Pr34 | ESI+ 419 |
| Pr8-9 | Pr8 | ESI+ 277 | Pr34-1 | Pr34 | ESI+ 452, 454 |
| Pr8-10 | Pr8 | ESI+ 316 | Pr34-2 | Pr34 | ESI+ 449 |
| Pr8-11 | Pr8 | ESI+ 277 | Pr34-3 | Pr34 | ESI+ 419 |
| Pr8-12 | Pr8 | ESI+ 295 | Pr34-4 | Pr34 | ESI+ 433 |
| Pr8-13 | Pr8 | ESI+ 307 | Pr34-5 | Pr34 | ESI+ 433 |
| Pr8-14 | Pr8 | ESI+ 307 | Pr35 | Pr35 | ESI+ 116 |
| Pr8-15 | Pr8 | ESI+ 330 | Pr35-1 | Pr35 | ESI+ 116 |
| Pr8-16 | Pr8 | ESI+ 293 | | | |

TABLE 20

| No. | Ref | Dat | No. | Ref | Dat |
|---|---|---|---|---|---|
| Ex1 | Ex1 | ESI+ 422 | Ex40 | Ex9 | ESI+ 368 |
| Ex2 | Ex1 | ESI+ 383 | Ex41 | Ex9 | ESI+ 372 |
| Ex3 | Ex1 | ESI+ 386 | Ex42 | Ex9 | ESI+ 372 |
| Ex4 | Ex1 | ESI+ 403 | Ex43 | Ex9 | APCI/ESI+ 368 |
| Ex5 | Ex1 | ESI+ 384 | Ex44 | Ex18 | ESI+ 397 |
| Ex6 | Ex1 | ESI+ 417 | Ex45 | Ex18 | ESI+ 354 |
| Ex7 | Ex1 | ESI+ 422 | Ex46 | Ex18 | ESI+ 382 |
| Ex8 | Ex1 | ESI+ 380 | Ex47 | Ex9 | ESI+ 397 |
| Ex9 | Ex9 | ESI+ 412 | Ex48 | Ex18 | ESI+ 393 |
| Ex10 | Ex9 | ESI+ 383 | Ex49 | Ex18 | ESI+ 382 |
| Ex11 | Ex9 | ESI+ 384 | Ex50 | Ex18 | ESI+ 372 |
| Ex12 | Ex9 | ESI+ 401 | Ex51 | Ex18 | ESI+ 405, 407 |
| Ex13 | Ex9 | ESI+ 457 | Ex52 | Ex18 | ESI+ 381 |
| Ex14 | Ex9 | ESI+ 389 | Ex53 | Ex18 | ESI+ 463 |
| Ex15 | Ex9 | ESI+ 414 | Ex54 | Ex18 | ESI+ 371 |
| Ex16 | Ex9 | ESI+ 428 | Ex55 | Ex18 | ESI+ 382 |
| Ex17 | Ex9 | ESI+ 445, 447 | Ex56 | Ex18 | ESI+ 401 |
| Ex18 | Ex18 | ESI+ 417, 419 | Ex57 | Ex18 | ESI+ 389 |
| Ex19 | Ex18 | ESI+ 424 | Ex58 | Ex18 | ESI+ 375 |
| Ex20 | Ex18 | ESI+ 401 | Ex59 | Ex18 | ESI+ 385 |
| Ex21 | Ex18 | ESI+ 408 | Ex60 | Ex18 | ESI+ 440 |
| Ex22 | Ex18 | ESI+ 423 | Ex61 | Ex18 | ESI+ 401 |
| Ex23 | Ex18 | ESI+ 401 | Ex62 | Ex18 | ESI+ 386 |
| Ex24 | Ex18 | ESI+ 401 | Ex63 | Ex18 | ESI+ 382 |
| Ex25 | Ex18 | ESI+ 422 | Ex64 | Ex18 | APCI/ESI+ 401 |
| Ex26 | Ex18 | ESI+ 387 | Ex65 | Ex18 | ESI+ 401 |
| Ex27 | Ex18 | ESI+ 403 | Ex66 | Ex18 | ESI+ 397 |
| Ex28 | Ex18 | ESI+ 439 | Ex67 | Ex18 | ESI+ 393 |
| Ex29 | Ex18 | ESI+ 407 | Ex68 | Ex18 | ESI+ 393 |
| Ex30 | Ex18 | ESI+ 442 | Ex69 | Ex69 | ESI+ 368 |
| Ex31 | Ex18 | ESI+ 451 | Ex70 | Ex69 | ESI+ 368 |
| Ex32 | Ex32 | ESI+ 417, 419 | Ex71 | Ex69 | ESI+ 368 |
| Ex33 | Ex33 | APCI/ESI+ 417 | Ex72 | Ex69 | ESI+ 382 |
| Ex34 | Ex1 | ESI+ 417, 419 | Ex73 | Ex69 | ESI+ 382 |
| Ex35 | Ex1 | ESI+ 383 | Ex74 | Ex69 | ESI+ 382 |
| Ex36 | Ex1 | ESI+ 384 | Ex75 | Ex69 | ESI+ 405, 407 |
| Ex37 | Ex1 | ESI+ 384 | Ex76 | Ex69 | ESI+ 405, 407 |
| Ex38 | Ex1 | ESI+ 398 | Ex77 | Ex69 | ESI+ 409 |
| Ex39 | Ex1 | ESI+ 397 | Ex78 | Ex18 | APCI/ESI+ 372 |

TABLE 21

| No. | Dat |
|---|---|
| Ex 1 | NMR1: 1.44-1.61 (2H, m), 1.72-1.83 (1H, m), 1.92-2.05 (1H, m), 2.75-2.91 (4H, m), 3.00-3.10 (2H, m), 3.60-3.76 (4H, m), 4.17-4.24 (1H, m), 4.57-4.65 (1H, m), 6.63 (1H, s), 6.82 (1H, s), 7.74 (1H, dd, J = 9.0, 4.8 Hz), 8.39 (1H, d, J = 8.7 Hz), 9.02 (1H, dd, J = 4.7, 1.4 Hz), 11.5 (1H, s), 13.1 (1H, brs) |
| Ex 7 | NMR1: 1.46-1.59 (2H, m), 1.72-1.81 (1H, m), 1.95-2.04 (1H, m), 2.78-2.90 (4H, m), 3.03-3.10 (2H, m), 3.61-3.75 (4H, m), 4.17-4.24 (1H, m), 4.58-4.64 (1H, m), 6.63 (1.6H, s), 6.82 (1H, s), 7.74 (1H, dd, J = 9.0, 4.8 Hz), 8.39 (1H, d, J = 9.0 Hz), 9.02 (1H, dd, J = 4.7, 1.5 Hz), 11.5 (1H, s), 13.1 (1.6H, brs) |
| Ex 9 | NMR1: 1.19 (12H, s), 2.78-2.86 (2H, m), 3.11 (2H, brs), 3.44 (4H, s), 3.63-3.68 (2H, m), 3.68-3.74 (2H, m), 6.83 (1H, brs), 8.41-8.47 (2H, m), 9.41 (1H, s), 11.29 (1H, s) |
| Ex 12 | NMR1: 1.15 (6H, d, J = 6.2 Hz), 2.35 (2H, dd, J = 12.6, 10.7 Hz), 2.76-2.86 (2H, m), 3.00-3.09 (2H, m), 3.54-3.73 (6H, m), 4.11-4.20 (2H, m), 6.69 (1H, brs), 7.74-7.83 (1H, m), 8.15-8.24 (1H, m), 8.33-8.38 (1H, m), 11.01 (1H, brs) |
| Ex 18 | NMR1: 1.15 (6H, d, J = 6.4 Hz), 2.39-2.54 (2H, m), 2.78-2.85 (2H, m), 3.08-3.19 (2H, m), 3.55-3.68 (4H, m), 3.68-3.74 (2H, m), 4.19 (2H, d, J = 11.9 Hz), 6.87 (1H, brs), 7.97 (1H, dd, J = 8.9, 2.7 Hz), 8.20 (1H, d, J = 8.9 Hz), 8.41 (1H, d, J = 2.5 Hz), 11.17 (1H, brs) |
| Ex 37 | NMR1: 1.17 (3H, d, J = 6.2 Hz), 1.61-1.72 (1H, m), 1.85-2.08 (3H, m), 2.75-2.86 (2H, m), 2.96-3.08 (2H, m), 3.22-3.34 (1H, m), 3.42-3.53 (1H, m), 3.56-3.76 (4H, m), 4.00 (3H, s), 4.06-4.18 (1H, m), 6.30 (1H, m), 7.29 (1H, d, J = 9.6 Hz), 8.28 (1H, d, J = 9.4 Hz), 11.3 (1H, s) |
| Ex 40 | NMR1: 1.19 (3H, d, J = 6.2 Hz), 1.71-1.82 (1H, m), 1.96-2.21 (3H, m), 2.46 (3H, s), 2.79-2.89 (2H, m), 3.16-3.96 (8H, m), 4.40 (1H, brs), 7.06 (1H, brs), 8.37 (1H, s), 9.24 (1H, s), 11.51 (1H, brs) |

TABLE 21-continued

| No. | Dat |
|---|---|
| Ex 55 | NMR1: 1.19 (3H, d, J = 6.2 Hz), 1.70-1.82 (1H, m), 1.95-2.20 (3H, m), 2.45 (3H, s), 2.48 (3H, s), 2.79-2.88 (2H, m), 3.60-3.69 (2H, m), 3.69-3.80 (2H, m), 3.81-4.14 (4H, m), 4.39 (1H, brs), 7.01 (1H, brs), 9.10 (1H, s), 11.35 (1H, brs) |
| Ex 70 | NMR1: 1.13-1.21 (3H, m), 1.40-1.54 (1H, m), 1.54-1.82 (5H, m), 2.86 (2H, brs), 3.28 (2H, brs), 3.60-3.70 (2H, m), 3.70-3.78 (2H, m), 4.12 (1H, brs), 7.13 (1H, brs), 8.41-8.51 (2H, m), 9.41 (1H, brs), 11.45 (1H, brs) |

TABLE 22

| No. | Dat |
|---|---|
| Ex 76 | NMR1: 1.48-1.64 (1H, m), 1.70-2.01 (3H, m), 2.73-2.87 (2H, m), 3.03-3.20 (2H, m), 3.35-3.47 (1H, m), 3.52-3.81 (6H, m), 3.90 (1H, brs), 4.70-4.89 (1H, m), 6.93 (1H, brs), 7.25-7.35 (3H, m), 7.55-7.62 (2H, m), 7.97 (1H, dd, J = 8.8, 2.6 Hz), 8.20 (1H, d, J = 8.7 Hz), 8.42 (1H, d, J = 2.5 Hz), 11.21 (1H, s) |
| Ex 78 | NMR1: 1.65-1.81 (2H, m), 1.85-2.04 (2H, m), 2.79-2.91 (2H, m), 3.07-3.21 (2H, m), 3.26-4.10 (8H, m), 4.79-5.02 (1H, m), 6.99 (1H, s), 7.77 (1H, dd, J = 9.0, 4.7 Hz), 8.40 (1H, d, J = 9.1 Hz), 9.04 (1H, d, J = 4.7 Hz), 11.64 (1H, s) |

INDUSTRIAL APPLICABILITY

A compound of the formula (I) or a salt thereof has a positive allosteric modulating activity (PAM activity) on an α7 nicotinic acetylcholine receptor (α7 nACh receptor), and can be expected as an agent for preventing or treating dementia, cognitive impairment, schizophrenia, Alzheimer's disease, CIAS, negative symptoms of schizophrenia, inflammatory diseases, or pain.

The invention claimed is:

1. A compound of formula (I):

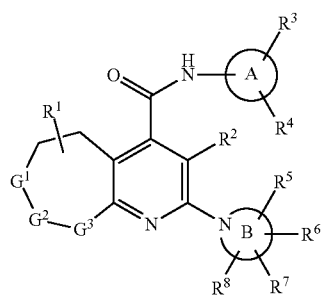

(I)

wherein:
$R^1$ is H or lower alkyl,
$R^2$ is H or CN,
any one of $G^1$, $G^2$, and $G^3$ is O, and the other two of $G^1$, $G^2$, and $G^3$ are $CH_2$,
ring A is aryl or nitrogen-containing heteroaryl,
ring B is cyclic amino,
$R^3$ and $R^4$ are the same or different and are H, halogen, lower alkyl, -lower alkylene-OH, halo-lower alkyl, —O-lower alkyl, —O-halo-lower alkyl, cycloalkyl, CN, OH, —N(lower alkyl)$_2$, or —C(=O)NH$_2$,
$R^5$, $R^6$, $R^7$ and $R^8$ are the same or different and are H, halogen, lower alkyl, halo-lower alkyl, —O-lower alkyl, or CN, or when $R^5$ and $R^6$ are bonded to the same carbon atom, then $R^5$ and $R^6$ optionally form cycloalkane or cyclic ether together with the carbon atom, and may form a spiro ring together with Ring B, or
ring B optionally forms 6,7-dihydro[1,3]oxazolo[4,5-c]pyridin-5(4H)-yl together with $R^5$ and $R^6$,
or a salt thereof.

2. The compound or salt thereof according to claim 1, wherein:
$R^1$ is H,
$R^2$ is H,
$G^1$ is O,
$G^2$ and $G^3$ are $CH_2$,
ring A is phenyl or nitrogen-containing heteroaryl,
ring B is 5- or 6-membered cyclic amino, and
$R^5$, $R^6$, $R^7$ and $R^8$ are the same or different and are H, halogen, lower alkyl, halo-lower alkyl, —O-lower alkyl, or CN.

3. The compound or salt thereof according to claim 2, wherein:
ring A is nitrogen-containing monocyclic heteroaryl,
$R^3$ is H or lower alkyl, and
$R^4$ is H, halogen, lower alkyl, -lower alkylene-OH, halo-lower alkyl, —O-lower alkyl, —O-halo-lower alkyl, cycloalkyl, CN, OH, —N(lower alkyl)$_2$, or —C(=O)NH$_2$.

4. The compound or salt thereof according to claim 3, wherein:
ring B, $R^5$, $R^6$, $R^7$, and $R^8$ together form a group of formula (II):

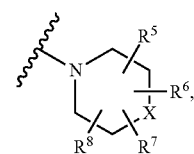

(II)

wherein:
X is $CH_2$, O, or a bond,
when X is $CH_2$, then $R^5$ and $R^6$ are optionally bonded to X, and
$R^5$, $R^6$, $R^7$, and $R^8$ are the same or different and are H, halogen, lower alkyl, or halo-lower alkyl.

5. The compound or salt thereof according to claim 4, wherein:
X is $CH_2$ or O.

6. The compound or salt thereof according to claim 4, wherein:
X is a bond.

7. The compound or salt thereof according to claim 5, wherein:

ring A is nitrogen-containing 6-membered heteroaryl having one or two nitrogen atoms as ring atoms, ring B, $R^5$, $R^6$, $R^7$, and $R^8$ together form a group of formula (III):

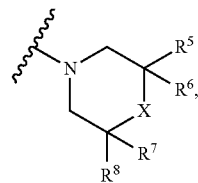

(III)

wherein:
$R^5$ is halogen or lower alkyl,
$R^6$ is H,
$R^7$ is H, and
$R^8$ is H or lower alkyl.

8. The compound or salt thereof according to claim 7, wherein:
ring A is pyridyl,
X is $CH_2$,
$R^5$ is halogen, and
$R^8$ is H.

9. The compound or salt thereof according to claim 7, wherein:
ring A is pyridyl,
X is O,
$R^5$ is lower alkyl, and
$R^8$ is lower alkyl.

10. The compound or salt thereof according to claim 6, wherein:
ring A is nitrogen-containing 6-membered heteroaryl having two nitrogen atoms as ring atoms,
ring B, $R^5$, $R^6$, $R^7$, and $R^8$ together form a group of formula (IV):

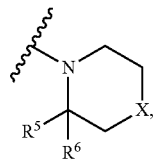

(IV)

wherein:
$R^5$ is halogen or lower alkyl,
$R^6$ is H,
$R^7$ is H, and
$R^8$ is H.

11. A compound or a salt thereof, which is a compound selected from the group consisting of:
N-(5-chloropyridin-2-yl)-2-[(2R,6S)-2,6-dimethylmorpholin-4-yl]-5,6,8,9-tetrahydrooxepino[4,5-b]pyridine-4-carboxamide,
N-(6-methoxypyridazin-3-yl)-2-[(2R)-2-methylpyrrolidin-1-yl]-5,6,8,9-tetrahydrooxepino[4,5-b]pyridine-4-carboxamide,
N-(6-methylpyrazin-2-yl)-2-[(2S)-2-methylpyrrolidin-1-yl]-5,6,8,9-tetrahydrooxepino[4,5-b]pyridine-4-carboxamide,
2-[(2R)-2-ethylmorpholin-4-yl]-N-(6-methylpyridin-3-yl)-5,6,8,9-tetrahydrooxepino[4,5-b]pyridine-4-carboxamide,
2-(4-fluoropiperidin-1-yl)-N-(pyridazin-3-yl)-5,6,8,9-tetrahydrooxepino[4,5-b]pyridine-4-carboxamide,
N-(5,6-dimethylpyrazin-2-yl)-2-[(2S)-2-methylpyrrolidin-1-yl]-5,6,8,9-tetrahydrooxepino[4,5-b]pyridine-4-carboxamide,
2-[(2S)-2-methylpiperidin-1-yl]-N-(pyridazin-3-yl)-5,6,8,9-tetrahydrooxepino[4,5-b]pyridine-4-carboxamide,
2-[(2S)-2-methylpiperidin-1-yl]-N-(pyrazin-2-yl)-5,6,8,9-tetrahydrooxepino[4,5-b]pyridine-4-carboxamide, and,
N-(5-chloropyridin-2-yl)-2-[(3S)-3-fluoropiperidin-1-yl]-5,6,8,9-tetrahydrooxepino[4,5-b]pyridine-4-carboxamide,
or a salt of said compound.

12. The compound or salt thereof according to claim 11, which is N-(5-chloropyridin-2-yl)-2-[(2R,6S)-2,6-dimethylmorpholin-4-yl]-5,6,8,9-tetrahydrooxepino[4,5-b]pyridine-4-carboxamide or a salt thereof.

13. The compound or salt thereof according to claim 11, which is N-(6-methoxypyridazin-3-yl)-2-[(2R)-2-methylpyrrolidin-1-yl]-5,6,8,9-tetrahydrooxepino[4,5-b]pyridine-4-carboxamide or a salt thereof.

14. The compound or salt thereof according to claim 11, which is N-(5-chloropyridin-2-yl)-2-[(3S)-3-fluoropiperidin-1-yl]-5,6,8,9-tetrahydrooxepino[4,5-b]pyridine-4-carboxamide or a salt thereof.

15. A pharmaceutical composition, comprising a compound or a salt thereof according to claim 1 and a pharmaceutically acceptable excipient.

16. A method for treating a disease or condition modulated by the stimulation of the α7 nACh receptor wherein said disease or condition is selected from the group consisting of dementia, cognitive impairment, schizophrenia, Alzheimer's disease, CIAS, negative symptoms of schizophrenia, inflammatory diseases, and pain, said method comprising administering an effective amount of a compound or a salt thereof according to claim 1 to a subject in need thereof.

* * * * *